US009695193B2

(12) United States Patent
Akabas et al.

(10) Patent No.: US 9,695,193 B2
(45) Date of Patent: Jul. 4, 2017

(54) INHIBITORS OF *PLASMODIUM FALCIPARUM* EQUILIBRATIVE NUCLEOSIDE TRANSPORTER TYPE I AS ANTI-PARASITIC COMPOUNDS

(71) Applicants: The Trustees of Columbia University in the City of New York, New York, NY (US); ALBERT EINSTEIN COLLEGE OF MEDICINE INC., New York, NY (US)

(72) Inventors: Myles Akabas, Scarsdale, NY (US); Ithiel James Frame, Bronx, NY (US); Donald W. Landry, New York, NY (US); Roman Deniskin, Bronx, NY (US); Shixian Deng, White Plains, NY (US); Alison Rinderspacher, Bronx, NY (US)

(73) Assignees: THE TRUSTEES OF COLUMBIA UNIVERSITY IN THE CITY OF NEW YORK, New York, NY (US); ALBERT EINSTEIN COLLEGE OF MEDICINE, INC., Bronx, NY (US)

( * ) Notice: Subject to any disclaimer, the term of this patent is extended or adjusted under 35 U.S.C. 154(b) by 0 days.

(21) Appl. No.: 14/898,846

(22) PCT Filed: Jun. 26, 2014

(86) PCT No.: PCT/US2014/044357
§ 371 (c)(1),
(2) Date: Dec. 16, 2015

(87) PCT Pub. No.: WO2014/210319
PCT Pub. Date: Dec. 31, 2014

(65) Prior Publication Data
US 2016/0122362 A1 May 5, 2016

Related U.S. Application Data

(60) Provisional application No. 61/839,527, filed on Jun. 26, 2013.

(51) Int. Cl.
C07D 498/04 (2006.01)
C07D 413/14 (2006.01)
A61K 31/517 (2006.01)
C07D 311/16 (2006.01)
C07D 417/14 (2006.01)
C07D 209/12 (2006.01)
C07D 239/88 (2006.01)
C07D 403/12 (2006.01)

(52) U.S. Cl.
CPC .......... *C07D 498/04* (2013.01); *A61K 31/517* (2013.01); *C07D 209/12* (2013.01); *C07D 239/88* (2013.01); *C07D 311/16* (2013.01); *C07D 403/12* (2013.01); *C07D 413/14* (2013.01); *C07D 417/14* (2013.01)

(58) Field of Classification Search
None
See application file for complete search history.

(56) References Cited

U.S. PATENT DOCUMENTS

2013/0022612 A1    1/2013 Sinnis

OTHER PUBLICATIONS

Winzeler, E.A. et al. Functional characterization of the *S. cerevisiae* genome by gene deletion and parallel analysis. Science 285, 901-6 (1999).
Janke, C. et al. A versatile toolbox for PCR-based tagging of yeast genes: new fluorescent proteins, more markers and promoter substitution cassettes. Yeast 21, 947-62 (2004).
Gari, E., Piedrafita, L., Aldea, M. & Herrero, E. A set of vectors with a tetracycline-regulatable promoter system for modulated gene expression in *Saccharomyces cerevisiae*. Yeast 13, 837-48 (1997).
Riegelhaupt, P.M. et al, Transport of purines and purine salvage pathway inhibitors by the Plasmodium falciparum equilibrative nucleoside transporter PfENT1. *Mol. Biochem. Parasitol.* 169, 40-9 (2010).
Westermann, B. & Neupert, W. Mitochondria-targeted green fluorescent proteins: convenient tools for the study of organelle biogenesis in *Saccharomyces cerevisiae*. Yeast 16, 1421-7 (2000).
Hill, J., Donald, K.A. & Griffiths, D.E. DMSO-enhanced whole cell yeast transformation. Nucleic Acids Res. 19, 5791 (1991).
Sheff, M.A. & Thorn, K.S. Optimized cassettes for fluorescent protein tagging in *Saccharomyces cerevisiae*. Yeast 21, 661-70 (2004).
Baldwin SA, Beal PR, Yao SY, King AE, Cass CE, et al. (2004) The equilibrative nucleoside transporter family, SLC29. Pflugers Arch 447: 735-743.
Pastor-Anglada M, Cano-Soldado P, Errasti-Murugarren E, Casado FJ (2008) SLC28 genes and concentrative nucleoside transporter (CNT) proteins. Xenobiotica 38: 972-994.
Carter NS, Yates P, Arendt CS, Boitz JM, Ullman B (2008) Purine and pyrimidine metabolism in Leishmania. Adv Exp Med Biol 625: 141-154.
Landfear SM, Ullman B, Carter NS, Sanchez MA (2004) Nucleoside and nucleobase transporters in parasitic protozoa. Eukaryot Cell 3: 245-254.
Cass CE, Young JD, Baldwin SA (1998) Recent advances in the molecular biology of nucleoside transporters of mammalian cells. Biochem Cell Biol 76: 761-770.
Cass CE, Young JD, Baldwin SA, Cabrita MA, Graham KA, et al. (1999) Nucleoside transporters of mammalian cells. Pharm Biotechnol 12: 313-352.
Cassera MB, Zhang Y, Hazleton KZ, Schramm VL (2011) Purine and pyrimidine pathways as targets in Plasmodium falciparum. Current topics in medicinal chemistry 11: 2103-2115.
El Bissati K, Zufferey R, Witola WH, Carter NS, Ullman B, et al. (2006) The plasma membrane permease PfNT1 is essential for purine salvage in the human malaria parasite Plasmodium falciparum. Proc Natl Acad Sci U S A 103: 9286-9291.

(Continued)

*Primary Examiner* — Heidi Reese
(74) *Attorney, Agent, or Firm* — Leason Ellis LLP

(57) ABSTRACT

Inhibitors of *Plasmodium falciparum* equilibrative nucleoside transporter type 1 are identified and methods of use as anti-parasitic compounds are provided.

9 Claims, 5 Drawing Sheets

(56) References Cited

OTHER PUBLICATIONS

Mlambo G, Kumar N. (2008). "Transgenic rodent Plasmodium berghei parasites as tools for assessment of functional immunogenicity and optimization of human malaria vaccines". Eukaryotic Cell 7 (11): 1875-9.
Mueller I, Zimmerman PA, Reeder JC (2007). "Plasmodium malariae and Plasmodium ovale—the "bashful" malaria parasites". Trends in Parasitology 23 (6): 278-83.
Collins WE (2012). "Plasmodium knowlesi: A malaria parasite of monkeys and humans". Annual Review of Entomology 57: 107-21.
Nadjm B, Behrens RH (2012). "Malaria: An update for physicians". Infectious Disease Clinics of North America 26 (2): 243-59.
Sarkar PK, Ahluwalia G, Vijayan VK, Talwar A (2009). "Critical care aspects of malaria". Journal of Intensive Care Medicine 25 (2): 93-103.
Baird JK (2013). "Evidence and implications of mortality associated with acute Plasmodium vivax malaria". Clinical Microbiology Reviews 26 (1): 36-57.
Arnott A, Barry AE, Reeder JC (2012). "Understanding the population genetics of Plasmodium vivax is essential for malaria control and elimination". Malaria Journal 11: 14.
Thompson, M J, Borsenberger, V, Louth, JC, Judd, KE, Chen, B (2009). "Design, Synthesis, and Structure-Activity Relationship of Indole-3-glyoxylamide Libraries Possessing Highly Potent Activity in a Cell Line Model of Prion Disease". Journal of Medicinal Chemistry 52 (23): 7503-7511.
Léval, A. & Jekö, J. An efficient procedure for the preparation of 4-methyl-2-thiocoumarins by the reaction of 4-methylcoumarins with Lawesson's reagent. J. Heterocyclic Chem. 42, 739-742 (2005).
Mezheritskii, V. V. et al. Polynuclear heterocyclic systems based on naphthalene-1,5-diol. I. Reaction of naphthalene-1,5-diol and its derivatives with β-dicarbonyl and α,β-unsaturated carbonyl compounds, Russ. J. Org. Chem. 42, 1458-1463 (2006).
Jagdale, A. R. & Sudalai, A., Co-catalyzed mild and chemoselective reduction of phenyl esters with NaBH4: a practical synthesis of (R)-tolterodine. Tetrahedron Lett. 49, 3790-3793 (2008).
Van Camp, J. A. et al., Preparation of 4-aryl-2-trifluoromethylbenzonitrile derivatives as androgen receptor antagonists for topical suppression of sebum production. Bioorg. Med. Chem. Lett. 17, 5529-5532 (2007).
Chembridge #6946484, pp. 1-2, Create date 2007-2010; [retrieved on Sep. 4, 2014], retrieved from the Internet; URL: http://www.hit2lead.com/result.asp?search=71684439.
Patel, K. et.al., Design, synthesis and biological evaluation of some novel 3-cinnamoyl-4-hydroxy-2H-chromen-2-ones as antimalarial agents, Med Chem. Res., 2012, vol. 21, pp. 1780-1784.
International Preliminary Report on Patentability in corresponding PCT Application No. PCT/US2014/044357, mailed Dec. 29, 2015.
International Search Report and Written Opinion in corresponding PCT Application No. pct/us2014/044357, mailed Dec. 9, 2014.

$Y^1$ = CH, N
$Y^2$ = CH, N
$R^3$ = H, alkyl, aryl
$R^4$ = H, alky, aryl, heteroaryl
$R^5$ = H, alky, aryl, heteroaryl

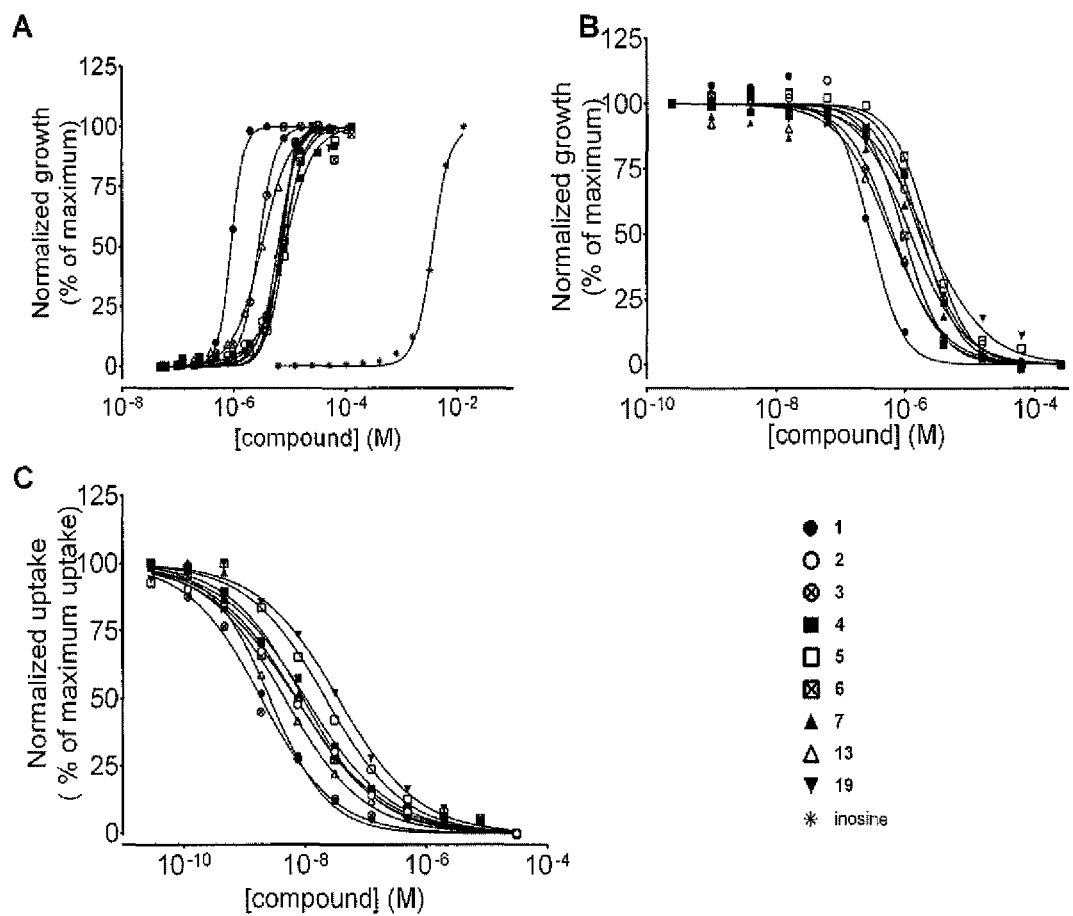
FIGURES 4A-C

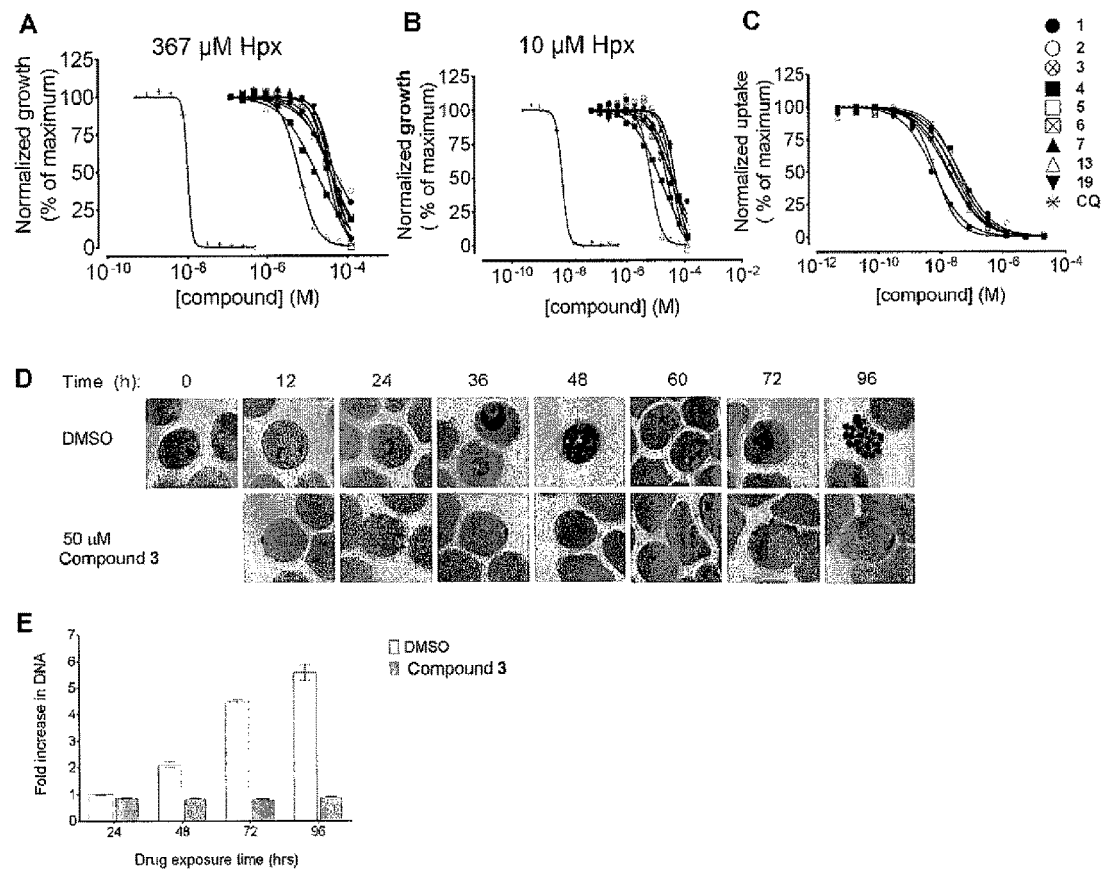
FIGURES 5A-E

INHIBITORS OF *PLASMODIUM FALCIPARUM* EQUILIBRATIVE NUCLEOSIDE TRANSPORTER TYPE I AS ANTI-PARASITIC COMPOUNDS

CROSS-REFERENCE TO RELATED APPLICATIONS

This application is a U.S. National Stage Application under 35 U.S.C. §371 of International Patent Application No. PCT/US2014/044357, filed Jun. 26, 2014, which claims priority to U.S. Provisional Patent Application Ser. No. 61/839,527, filed Jun. 26, 2013, each of which is incorporated herein by reference in its entirety.

STATEMENT OF GOVERNMENT SUPPORT

This invention was made with government support under grant number T32-GM007288 awarded by the National Institutes of Health. The government has certain rights in this invention.

FIELD OF THE INVENTION

The present invention relates to inhibitors of Equilibrative Nucleoside Transporter (ENT) and their use in methods of treatment or prevention of infection, or inhibiting the growth of parasitic auxotrophs, including *Plasmodium, Giardia, Trichomonas, Leishmania, Trypanosoma*, or *Leptomonas* species. In certain aspects, the infection is malaria and the parasite is *Plasmodium falciparum*.

BACKGROUND OF THE INVENTION

*Plasmodium*, a genus of parasitic protozoans of the sporozoan subclass Coccidia (phylum Apicomplexa) are the causative organisms of malaria. In humans, malaria is caused by *P. falciparum, P. malariae, P. ovale, P. vivax* and *P. knowlesi*. (Mueller et al. 2007 and Collins (2012)). Among those infected, *P. falciparum* is the most common species identified (~75%) followed by *P. vivax* (~20%) (Nadjm and Behrens 2012). Although *P. falciparum* traditionally accounts for the majority of deaths, (Sarkar et al. 2009) recent evidence suggests that *P. vivax* malaria is associated with potentially life-threatening conditions (Baird J K (2013)). *P. vivax* proportionally is more common outside of Africa (Arnott et al. 2012). There have been documented human infections with several species of *Plasmodium* from higher apes; however, with the exception of *P. knowlesi*—a zoonotic species that causes malaria in macaques—these are mostly of limited public health importance.

*P. falciparum*, which is found worldwide in tropical and subtropical areas. It is estimated that every year approximately 1 million people are killed by *P. falciparum*, especially in Africa where this species predominates. *P. falciparum* can cause severe malaria because it multiples rapidly in the blood, and can thus cause severe blood loss (anemia). In addition, the parasite infected red blood cells can clog small blood vessels. When this occurs in the brain, cerebral malaria results, a complication that can be fatal.

*P. vivax*, which is found mostly in Asia, Latin America, and in some parts of Africa. Because of the population densities especially in Asia it is probably the most prevalent human malaria parasite. *P. vivax* (as well as *P. ovale*) has dormant liver stages ("hypnozoites") that can activate and invade the blood ("relapse") several months or years after the infecting mosquito bite.

*P. ovale* is found mostly in Africa (especially West Africa) and the islands of the western Pacific. It is biologically and morphologically very similar to *P. vivax*. However, differently from *P. vivax*, it can infect individuals who are negative for the Duffy blood group, which is the case for many residents of sub-Saharan Africa. This explains the greater prevalence of *P. ovale* (rather than *P. vivax*) in most of Africa.

*P. malariae*, found worldwide, is the only human malaria parasite species that has a quartan cycle (three-day cycle). (The three other species have a tertian, two-day cycle.) If untreated, *P. malariae* causes a long-lasting, chronic infection that in some cases can last a lifetime. In some chronically infected patients *P. malariae* can cause serious complications such as the nephrotic syndrome.

*P. knowlesi* is found throughout Southeast Asia as a natural pathogen of long-tailed and pig-tailed macaques. It has recently been shown to be a significant cause of zoonotic malaria in that region, particularly in Malaysia. *P. knowlesi* has a 24-hour replication cycle and so can rapidly progress from an uncomplicated to a severe infection; fatal cases have been reported.

In addition to these *Plasmodium*-mediated diseases, additional parasitic diseases are caused by protozoa as *Leishmania, Trypanosoma, Entamoeba, Giardia, Naegleria*, and *Trichomonas*. Taken together, these protozoan parasitic diseases are responsible for more than three millions deaths annually throughout the world. The WHO has declared six major diseases namely leishmaniasis, malaria, amoebiasis, filariasis, Chagas disease and schistosomiasis in its Special Programme for Research and Training in Tropical Diseases. Selectivity of an antiparasitic compound should target as its mode of specific inhibition an aspect that leaves host processes unaffected.

Currently, Artemisinin combination therapy (ACT) is the treatment of choice for *P. falciparum* malaria. Resistance to ACT therapy has recently been documented in Southeast Asia. It is likely only a matter of time before ACT resistance spreads and diminishes its efficacy as a first line therapy for malaria. Thus, it is imperative to identify and develop novel antimalarial therapies to treat the hundreds of millions of people infected by malaria each year. There is also a need for drugs that can be taken prophylactically when travelling to malaria endemic regions. Of note, some of the medicines currently available for prophylaxis of travelers to malaria endemic regions have significant side effects or are not suitable for use by children or pregnant woman. Thus, improved drugs are needed to address these unmet needs.

Some eukaryotic parasites, such as *Plasmodium* species that cause malaria, *Leshmania* species that cause leshmaniasis, *Trypanasoma* species that cause African sleeping sickness and Chagas disease and *Toxoplasma gondii* that causes toxoplasmosis, are purine auxotrophs, unable to perform de novo purine biosynthesis (Carter, N. S. et al. (2008); Landfear, S. M. et al. (2004); Cass, C. E. et al. (1998); Cass, C. E. et al. (1999); and Cassera, M. B. et al. (2011)). Because nucleobases and nucleosides are impermeable through phospholipid cell membranes, cells use Equilibrative Nucleoside Transporters (ENTs) and Concentrative Nucleoside Transporters (CNTs) to import and export purines and pyrimidines (Baldwin, S. A. et al. (2004), and Pastor-Anglada, M. et al. (2008)). The parasites rely on purine import via ENTs, and possibly CNTs, to supply purines needed for DNA synthesis and other cellular processes. The imported purines are processed through the purine salvage pathway to generate the specific purines required by the cell.

Blocking purine import will have inhibitory or cytotoxic effects on these parasites. For example, knockout of the Plasmodium falciparum Equilibrative Nucleoside Transporter Type 1 (PfENT1) results in parasites that are not viable during in vitro culture in growth media containing physiological purine concentrations found in normal human blood (El Bissati, K. et al. (2006)).

The present invention discloses ENT inhibitors and their use as anti-parasitic compounds.

SUMMARY OF THE INVENTION

In accordance with the present invention there is provided compounds of Formula I and methods for treating a parasitic auxotrophic infection in a patient, or for inhibiting a parasitic auxotrophic infection in a patient, comprising administering to the patient any one of the compounds having the formula:

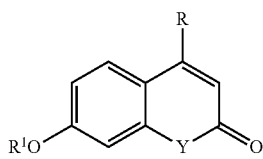

I wherein Y is selected from O, NH, and S;
R is selected from C1-C10 alkyl and aryl;
$R^1$ is selected from C1-C10 alkyl and optionally substituted benzyl; or a pharmaceutically acceptable salt thereof.
A preferred group of compounds of formula I are those wherein Y is O.
In a further embodiment, preferred compounds of the invention or a pharmaceutically acceptable salt thereof are:
4-methyl-7-[(3,4,5-trimethoxybenzyl)oxy]-2H-chromen-2-one,
4-methyl-7-[(4-chlorobenzyl)oxy]-2H-chromen-2-one,
4-methyl-7-[(4-fluorobenzyl)oxy]-2H-chromen-2-one,
4-methyl-7-[(4-methoxybenzyl)oxy]-2H-chromen-2-one,
4-methyl-7-[(3,5-dimethoxybenzyl)oxy]-2H-chromen-2-one,
4-butyl-7-[(3,4,5-trimethoxybenzyl)oxy]-2H-chromen-2-one,
4-methyl-7-[(4-methylbenzyl)oxy]-2H-chromen-2-one, and
4-methyl-7-benzyl-oxy-2H-chromen-2-one.

In accordance with the present invention there are provided compounds of Formula II and methods for treating a parasitic auxotrophic infection in a patient or for inhibiting a parasitic auxotrophic infection in a patient, comprising administering to the patient any one of the compounds having the formula:

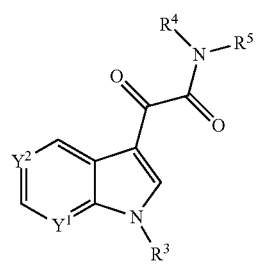

II wherein
$Y^1$ is selected from CH and N;
$Y^2$ is selected from CH and N;
$R^3$ is selected from H, C1-C10 alkyl, and aryl;
$R^4$ is selected from H, C1-C10 alkyl, aryl, and heteroaryl;
$R^5$ is selected from H, C1-C10 alkyl, aryl, and heteroaryl, or a pharmaceutically acceptable salt thereof.
Preferred compounds of the invention or a pharmaceutically acceptable salt thereof include:
2-(1-methyl-1H-indol-3-yl)-2-oxo-N-[4-(pyrrolidin-1-ylcarbonyl)phenyl]acetamide.

In accordance with the present invention there are provided compounds of Formula III and methods for treating a parasitic auxotrophic infection in a patient or for inhibiting a parasitic auxotrophic infection of a patient, comprising administering to the patient any one of the compounds having the formula:

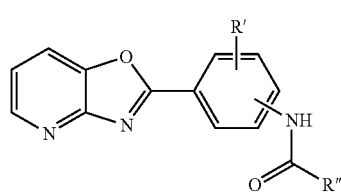

III wherein R' is selected from H and halogen;
R" is selected from

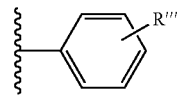

and thienyl;
R''' is H, halogen and alkoxy;
or a pharmaceutically acceptable salt thereof
Preferred compounds of the invention or a pharmaceutically acceptable salt thereof include:
2-bromo-N-(4-[1,3]oxazolo[4,5-b]pyridin-2-ylphenyl)benzamide,
3-fluoro-N-(3-[1,3]oxazolo[4,5-b]pyridin-2-ylphenyl)benzamide,
2-methoxy-N-(3-[1,3]oxazolo[4,5-b]pyridin-2-ylphenyl)benzamide, and
N-(4-chloro-3-[1,3]oxazolo[4,5-b]pyridin-2-ylphenyl)-2-thiophenecarboxamide.

In certain embodiments, the invention relates to a method of treating, preventing, or inhibiting a parasitic auxotrophic infection in a patient, comprising administering to the patient a compound having the formula according to Formula I, II, III, Table 1 or Table 2.

In yet additional embodiments, the invention relates to a pharmaceutical composition comprising a) pharmaceutically effective amount of a compound of Formula I, II or III, Table 1 or Table 2, or a pharmaceutically acceptable salt, solvate, poly-morph, tautomer or prodrug thereof. In certain embodiments, the compound further comprises a pharmaceutically acceptable carrier, diluent, excipient and/or adjuvant.

In yet additional embodiments, the invention relates to a method of treating, preventing, or inhibiting a parasitic auxotrophic infection in a patient, comprising administering a pharmaceutically effective amount of a compound of Formula I, II or III, Table 1 or Table 2.

In certain embodiments, the parasitic auxotroph is a *Plasmodium, Giardia, Trichomonas, Leishmania, Trypanosoma,* or *Leptomonas* species. In yet additional embodiments, the infection is malaria and the parasite is *Plasmodium falciparum.*

In certain embodiments, the invention relates to a method for inhibiting an Equilibrative Nucleoside Transporter (ENT) of a *Plasmodium* species comprising contacting the *Plasmodium* species with a compound of Formula I, II or III, Table 1 or Table 2, in an amount effective to inhibit the ENT of the *Plasmodium* species. In certain embodiments, the ENT is an ENT1, ENT2, ENT3, or ENT4. In certain embodiments, the ENT is an ENT1.

In yet additional embodiments, the parasite is a *P. falciparum, P. berghei, P. vivax, P. ovale, P. malariae* or *P. knowlesi*. In yet additional embodiments, the parasite is a *Plasmodium falciparum.*

In yet additional embodiments, the compound is 2-(1-methyl-1H-indol-3-yl)-2-oxo-N-[4-(pyrrolidin-1-ylcarbonyl)phenyl]acetamide or N-(4-chloro-3-[1,3]oxazolo[4,5-b]pyridin-2-ylphenyl)-2-thiophenecarboxamide.

In yet additional embodiments, the invention relates to a compound of Formula I, II or III, Table 1 or Table 2, or a pharmaceutically acceptable salt, solvate, poly-morph, tautomer or prodrug thereof, for use as a medicament. In certain embodiments, the medicament inhibits an Equilibrative Nucleoside Transporter (ENT).

In yet additional embodiments, the invention relates to the use of a compound of Formula I, II or III, Table 1 or Table 2, or a pharmaceutically acceptable salt, solvate, poly-morph, tautomer or prodrug thereof in the preparation of a pharmaceutical composition for inhibiting Equilibrative Nucleoside Transporter (ENT). In certain embodiments, the ENT is an ENT1.

In yet additional embodiments, the invention relates to the of a compound of Formula I, II or III, Table 1 or Table 2, or a pharmaceutically acceptable salt, solvate, poly-morph, tautomer or prodrug thereof in the preparation of a pharmaceutical composition for the treatment or prophylaxis of a disorder or disease mediated by infection with a parasitic purine auxotroph. In certain embodiments, the parasitic auxotroph is selected from the genera *Plasmodium, Giardia, Trichomonas, Leishmania, Trypanosoma, Crithidia, Herpetomonas, Leptomonas, Histomonas, Eimeria, Isopora,* and *Neospora*. In yet additional embodiments, the parasitic purine auxotroph is *Plasmodium falciparum*. In further embodiments, the disorder or disease is selected from the group consisting of malaria, (including cerebral malaria), leishmaniasis, African sleeping sickness, Chagas disease, and toxoplasmosis.

In certain embodiments, the invention relates to a method of the treatment or prophylaxis disorder or disease mediated by infection with a parasitic purine auxotroph, comprising administering to a patient in need thereof a therapeutically effective amount of the compound of Formula I, II or III, Table 1 or Table 2, or the pharmaceutical composition thereof. In certain embodiments, the disorder or disease is malaria. In yet additional embodiments, the disorder or disease is one or more of selected from the group consisting of malaria, leishmaniasis, African sleeping sickness, Chagas disease, and toxoplasmosis.

In yet additional embodiments, the compound is N,N'-1,3-benzothiazole-2,6-diyldi (2-furamide); 2-bromo-N-(4-[1,3]oxazolo[4,5-b]pyridin-2-ylphenyl)benzamide;

4-methyl-7-[(3,4,5-trimethoxybenzyl)oxy]-2H-chromen-2-one;

N-{4-[5-(2-furyl)-1,3,4-oxadiazol-2-yl]phenyl}-2-furamide;

2-(1-methyl-1H-indol-3-yl)-2-oxo-N-[4-(pyrrolidin-1-ylcarbonyl)phenyl]acetamide;

3-fluoro-N-(3-[1,3]oxazolo[4,5-b]pyridin-2-ylphenyl)benzamide;

2-methoxy-N-(3-[1,3]oxazolo[4,5-b]pyridin-2-ylphenyl) benzamide;

2-[2-(2-methylphenyl)vinyl]-4(3H)-quinazolinone; or

N-(4-chloro-3-[1,3]oxazolo[4,5-b]pyridin-2-ylphenyl)-2-thiophenecarboxamide.

In yet additional embodiments, the patient is a mammal.

BRIEF DESCRIPTION OF THE DRAWINGS

FIGS. 4A-C are graphs showing the validation of selected compounds identified as *Plasmodium falciparum* Equilibrative Nucleoside Transporter Type I (PfENT1) inhibitors in the high-throughput screen (HTS). FIG. 4A shows the concentration-dependent rescue of PfENT1-HA-CO-expressing fui1Δ yeast from 5-FUrd induced death with the nine compounds from Table 1. FIG. 4B shows the concentration-dependent growth inhibition of purine auxotrophic yeast expressing PfENT1-CO in adenosine medium with the nine compounds from Table 1. FIG. 4C shows the concentration-dependent inhibition of [$^3$H]adenosine uptake into PfENT1-CO expressing yeast over 15 minutes with the compounds from Table 1. The means values from single experiments are shown. In the key, CQ=chloroquine, and the Table 1 compounds are referenced as symbols indicating HTS rank #1-7, 13, and 19.

FIGS. 5A-E are graphs and images reflecting the inhibitory effects of selected PfENT1 inhibiting compounds with *P. falciparum*. FIGS. 5A-C are graphs illustrating the inhibitory effects of selected PfENT1 inhibiting compounds with *P. falciparum*. FIG. 5A shows concentration-dependent inhibition of *P. falciparum* 3D7 strain growth with nine selected compounds shown in Table 1, in the presence of extracellular hypoxanthine at a concentration of 367 μM or 10 μM (FIG. 5B). FIG. 5C shows concentration-dependent inhibition of [$^3$H]adenosine uptake into trophozoite-stage *P. falciparum* 3D7culture over 15 minutes with the nine selected compounds shown in Table 1. FIG. 5D shows stained cultures illustrating parasite morphology for compound 3 (ChemBridge #6946484) compared to DMSO treated *P. falciparum* 3D7cultures at the indicated times. FIG. 5E shows graphs illustrating DNA quantification for compound 3 (ChemBridge #6946484) compared to DMSO treated *P. falciparum* 3D7cultures at the indicated times.

DETAILED DESCRIPTION OF THE INVENTION

Figure 1:
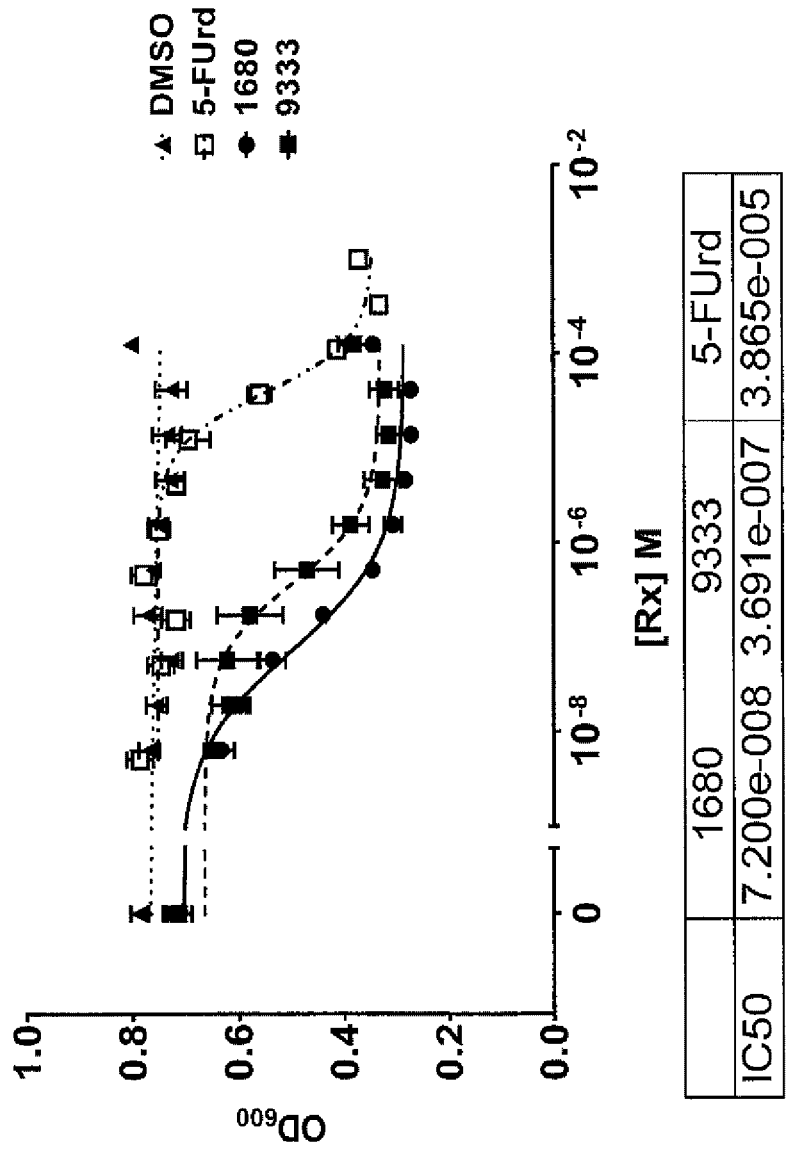
FIG. 1 is a graph showing the concentration-response relationship for the ChemBridge compounds #9039333 and #9011680 using growth inhibition of PfENT1-expressing ade2Δ yeast.

This invention provides a method for treating a parasitic auxotrophic infection in a patient or for inhibiting a parasitic auxotrophic infection in a patient, comprising administering to the patient a compound having any one of the formulas shown in Table 1.

TABLE 1

Structures and IC$_{50}$s in the yeast and parasite growth and [$^3$H] adenosine uptake assays for the nine compounds selected from the High-Throughput Screen. These compounds are the top seven hits (HTS rank #1-7), along with compound HTS #19 and compound HTS#13, which is th top quinazolinone from the screen.

| HTS Rank # | Structure | Compound Name ChemBridge # | IC$_{50}$ 5-FUrd growth rescue of fui1Δ::PfENT1-HA-CO (μM) | IC$_{50}$ ade2Δ + PfENT1-CO adenosine growth inhibition (μM) | IC$_{50}$ [$^3$H]-adenosine uptake into ade2Δ + PfENT1-CO yeast (nM) | IC$_{50}$ [$^3$H]-adenosine uptake into 3D7 parasites (nM) |
|---|---|---|---|---|---|---|
| 1 | 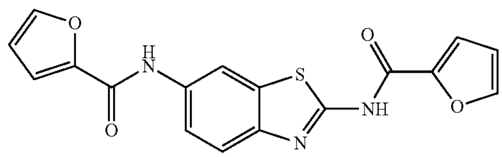 [SMILES: O=C(Nc1ccc2nc(NC(=O)c3ccco3)sc2c1)c1ccco1] | N,N'-1,3-benzothiazole-2,6-diyldi(2-furamide) 9001893 | 0.8 ± 0.0 | 0.2 ± 0.1 | 3.0 ± 1.3 | 5.4 ± 2.9 |
| 2 | 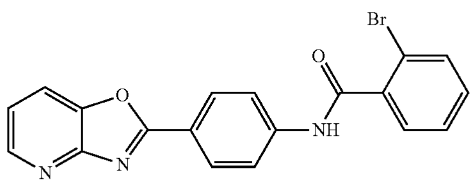 [SMILES: O=C(Nc1ccc(-c2nc3ncccc3o2)cc1)c1ccccc1Br] | 2-bromo-N-(4-[1,3]oxazolo[4,5-b]pyridin-2-ylphenyl)benzamide 6718896 | 6.0 ± 1.7 | 2.1 ± 0.9 | 10.1 ± 8.4 | 28.0 ± 12.3 |
| 3 | 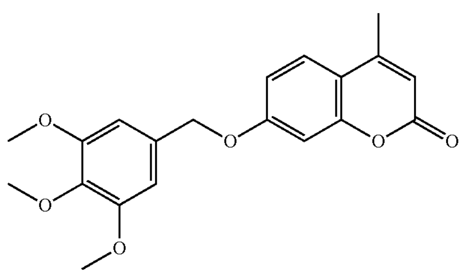 [SMILES: COc1cc(COc2ccc3c(C)cc(=O)oc3c2)cc(OC)c1OC] | 4-methyl-7-[(3,4,5-trimethoxybenzyl)oxy]-2H-chromen-2-one 6946484 | 2.3 ± 0.9 | 0.6 ± 0.1 | 2.4 ± 1.5 | 6.4 ± 3.0 |
| 4 | 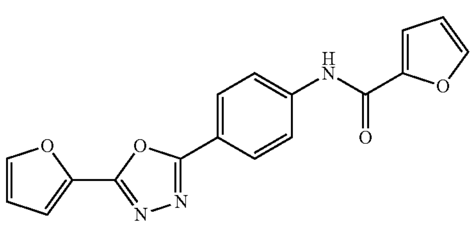 [SMILES: O=C(Nc1ccc(-c2nnc(-c3ccco3)o2)cc1)c1ccco1] | N-(4-[5-(2-furyl)-1,3,4-oxadiazol-2-yl]phenyl}-2-furamide 6081106 | 5.7 ± 0.8 | 1.7 ± 0.4 | 13.7 ± 7.5 | 45.8 ± 24.1 |
| 5 | 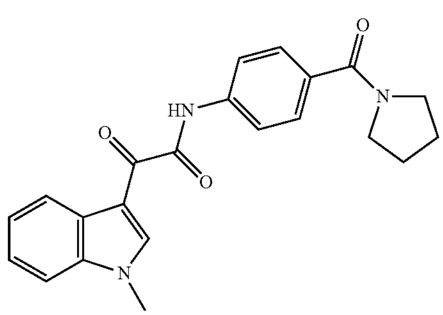 [SMILES: Cn1cc(C(=O)C(=O)Nc2ccc(C(=O)N3CCCC3)cc2)c2ccccc21] | 2-(1-methyl-1H-indol-3-yl)-2-oxo-N-[4-(pyrrolidin-1-ylcarbonyl)phenyl]acetamide 9039333 | 6.5 ± 1.5 | 2.0 ± 0.01 | 22.7 ± 7.2 | 38.6 ± 20.1 |

TABLE 1-continued

Structures and IC$_{50}$s in the yeast and parasite growth and [$^3$H] adenosine uptake assays for the nine compounds selected from the High-Throughput Screen. These compounds are the top seven hits (HTS rank #1-7), along with compound HTS #19 and compound HTS#13, which is th top quinazolinone from the screen.

| HTS Rank # | Structure | Compound Name ChemBridge # | IC$_{50}$ 5-FUrd growth rescue of fui1Δ::PfENT1-HA-CO (μM) | IC$_{50}$ ade2Δ + PfENT1-CO adenosine growth inhibition (μM) | IC$_{50}$ [$^3$H]-adenosine uptake into ade2Δ + PfENT1-CO yeast (nM) | IC$_{50}$ [$^3$H]-adenosine uptake into 3D7 parasites (nM) |
|---|---|---|---|---|---|---|
| 6 | 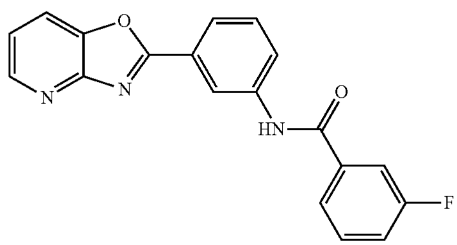 [SMILES: O=C(Nc1cccc(-c2nc3ncccc3o2)c1)c1cccc(F)c1] | 3-fluoro-N-(3-[1,3]oxazolo[4,5-b]pyridin-2-ylphenyl)benzamide 9011026 | 5.7 ± 1.3 | 1.1 ± 0.1 | 9.6 ± 7.4 | 19.8 ± 12.9 |
| 7 | 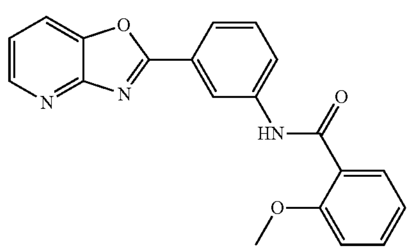 [SMILES: COc1ccccc1C(=O)Nc1cccc(-c2nc3ncccc3o2)c1] | 2-methoxy-N-(3-[1,3]oxazolo[4,5-b]pyridin-2-ylphenyl)benzamide 6736283 | 6.4 ± 0.9 | 1.6 ± 0.01 | 10.9 ± 6.8 | 24.8 ± 17.4 |
| 13 | 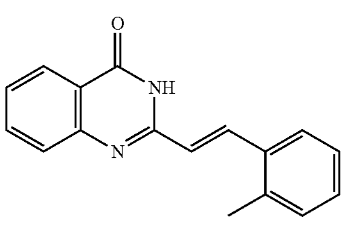 [SMILES: Cc1ccccc1/C=C/c1nc2ccccc2c(=O)[nH]1] | 2-[2-(2-methylphenyl)vinyl]-4(3H)-quinazolinone 6517398 | 4.7 ± 2.9 | 0.6 ± 0.1 | 3.09 ± 1.6 | 21.6 ± 14.2 |
| 19 | 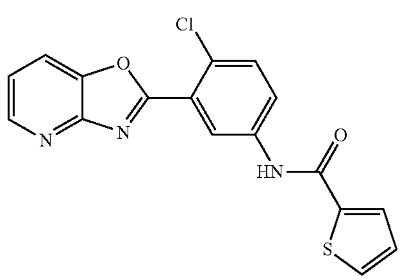 [SMILES: O=C(Nc1ccc(Cl)c(-c2nc3ncccc3o2)c1)c1cccs1] | N-(4-chloro-3-[1,3]oxazolo[4,5-b]pyridin-2-ylphenyl)-2-thiophenecarboxamide 9011680 | 5.4 ± 0.8 | 1.7 ± 0.2 | 38.4 ± 16.5 | 17.9 ± 12.7 |

Mean ± SD are shown, N ≥ 3 biological replicates for all data.
HTS Rank # is based on efficacy in the primary HTS.

TABLE 2

171 High Throughput Screen HITS

| Rank # | Avg Normalized % maximal activity | ChemBridge compound ID# | MW | Mol Name | Structure |
|---|---|---|---|---|---|
| 1 | 97.22 | 9001893 | 353.4 | N,N'-1,3-benzothiazole-2,6-diyldi(2-furamide) | 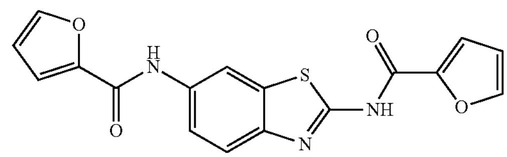 [SMILES: O=C(Nc1ccc2nc(NC(=O)c3ccco3)sc2c1)c1ccco1] |
| 2 | 91.94 | 6718896 | 394.2 | 2-bromo-N-(4-[1,3]oxazolo[4,5-b]pyridin-2-ylphenyl)benzamide | 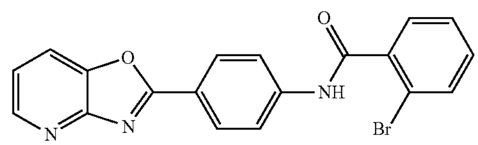 [SMILES: O=C(Nc1ccc(-c2nc3ncccc3o2)cc1)c1ccccc1Br] |
| 3 | 84.71 | 6946484 | 356.4 | 4-methyl-7-[(3,4,5-trimethoxybenzyl)oxy]-2H-chromen-2-one | 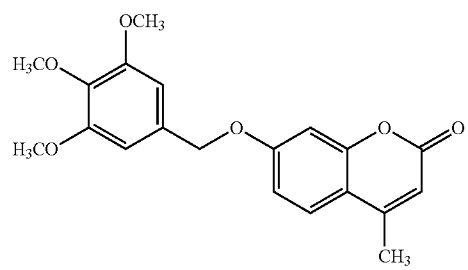 [SMILES: COc1cc(COc2ccc3c(C)cc(=O)oc3c2)cc(OC)c1OC] |
| 4 | 74.03 | 6081106 | 321.3 | N-{4-[5-(2-furyl)-1,3,4-oxadiazol-2-yl]phenyl}-2-furamide | 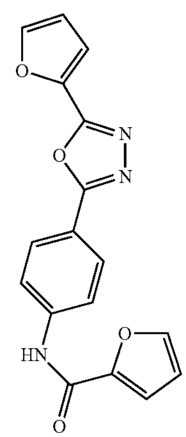 [SMILES: O=C(Nc1ccc(-c2nnc(-c3ccco3)o2)cc1)c1ccco1] |
| 5 | 64.07 | 9039333 | 375.4 | 2-(1-methyl-1H-indol-3-yl)-2-oxo-N-[4-(pyrrolidin-1-ylcarbonyl)phenyl]acetamide | 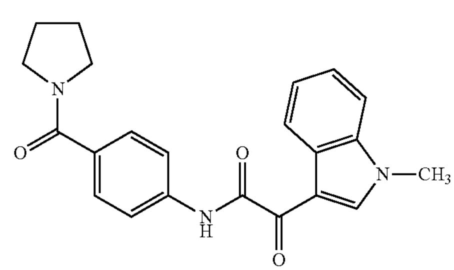 [SMILES: Cn1cc(C(=O)C(=O)Nc2ccc(C(=O)N3CCCC3)cc2)c2ccccc21] |

TABLE 2-continued

171 High Throughput Screen HITS

| Rank # | Avg Normalized % maximal activity | ChemBridge compound ID# | MW | Mol Name | Structure |
|---|---|---|---|---|---|
| 6 | 59.06 | 9011026 | 333.3 | 3-fluoro-N-(3-[1,3]oxazolo[4,5-b]pyridin-2-ylphenyl)benzamide | 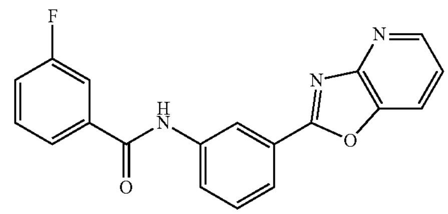 [SMILES: O=C(Nc1cccc(-c2nc3ncccc3o2)c1)c1cccc(F)c1] |
| 7 | 55.05 | 6736283 | 345.4 | 2-methoxy-N-(3-[1,3]oxazolo[4,5-b]pyridin-2-ylphenyl)benzamide | 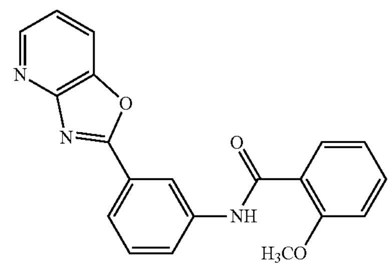 [SMILES: COc1ccccc1C(=O)Nc1cccc(-c2nc3ncccc3o2)c1] |
| 8 | 54.23 | 7993021 | 372.8 | 2-(2-chlorophenoxy)-N-[4-(1-piperidinylcarbonyl)phenyl]acetamide | 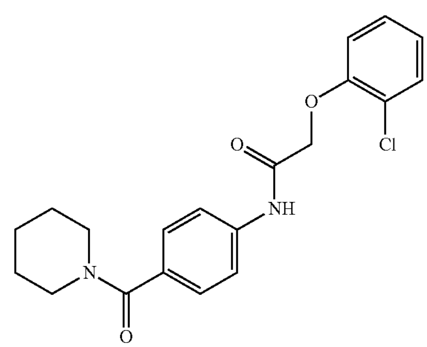 [SMILES: O=C(COc1ccccc1Cl)Nc1ccc(C(=O)N2CCCCC2)cc1] |
| 9 | 54.12 | 6838528 | 361 | N-{3-[5-(2-furyl)-1,3,4-oxadiazol-2-yl]phenyl}-3-methoxybenzamide | 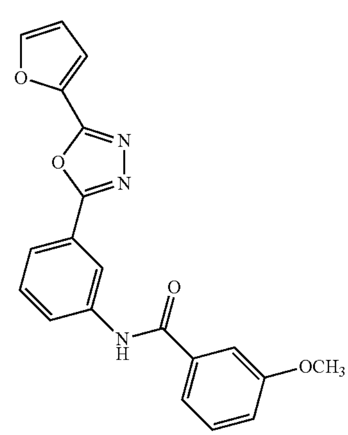 [SMILES: COc1cccc(C(=O)Nc2cccc(-c3nnc(-c4ccco4)o3)c2)c1] |

TABLE 2-continued

171 High Throughput Screen HITS

| Rank # | Avg Normalized % maximal activity | ChemBridge compound ID# | MW | Mol Name | Structure |
|---|---|---|---|---|---|
| 10 | 45.82 | 7240481 | 379.9 | 2-{[(3-chloro-1-benzothien-2-yl)carbonyl]amino}-N,N,4-trimethyl-1,3-thiazole-5-carboxamide | 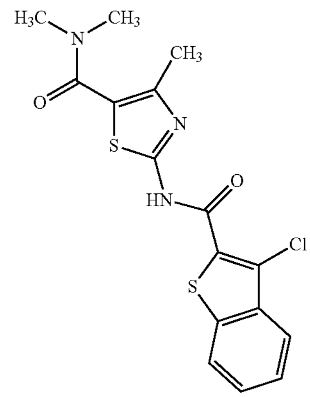 [SMILES: Cc1nc(NC(=O)c2sc3ccccc3c2Cl)sc1C(=O)N(C)C] |
| 11 | 32.85 | 6770368 | 305.3 | N-(3-[1,3]oxazolo[4,5-b]pyridin-2-ylphenyl)-2-furamide | 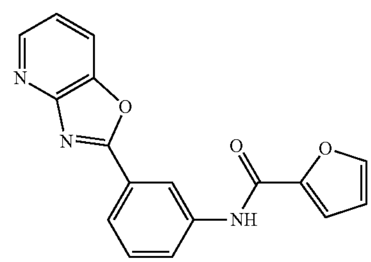 [SMILES: O=C(Nc1cccc(-c2nc3ncccc3o2)c1)c1ccco1] |
| 12 | 31.72 | 9008896 | 334.3 | 4-methyl-7-[(5-phenyl-1,3,4-oxadiazol-2-yl)methoxy]-2H-chromen-2-one | 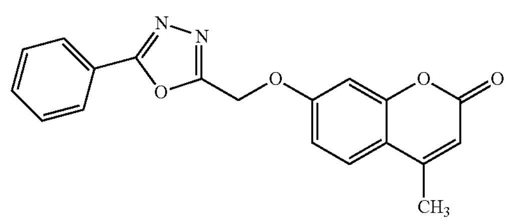 [SMILES: Cc1cc(=O)oc2cc(OCc3nnc(-c4ccccc4)o3)ccc12] |
| 13 | 24.69 | 6517398 | 262.3 | 2-[2-(2-methylphenyl)vinyl]-4(3H)-quinazolinone | 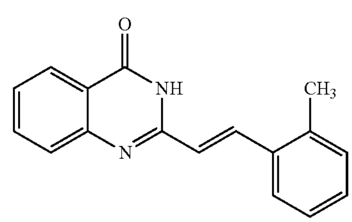 [SMILES: Cc1ccccc1/C=C/c1nc2ccccc2c(=O)[nH]1] |
| 14 | 24.47 | 7925013 | 321.3 | N-(4-{[(4-methyl-2-pyridinyl)amino]carbonyl}phenyl)-2-furamide | 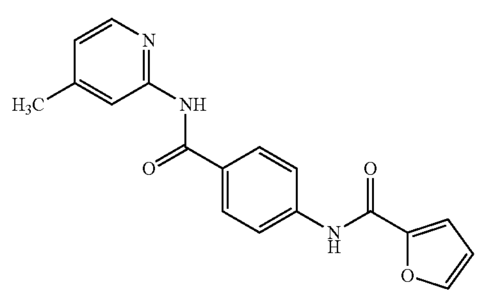 [SMILES: Cc1ccnc(NC(=O)c2ccc(NC(=O)c3ccco3)cc2)c1] |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 15 | 24.18 | 9010614 | 356.4 | N-[2-methoxy-5-(2-quinoxafinyl)phenyl]isonicotinamide | 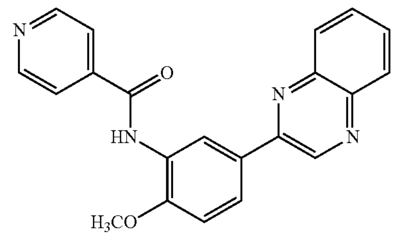 [SMILES: COc1ccc(-c2cnc3ccccc3n2)cc1NC(=O)c1ccncc1] |
| 16 | 23.87 | 6783000 | 345.4 | 4-methoxy-N-(3-[1,3]oxazolo[4,5-b]pyridin-2-ylphenyl)benzamide | 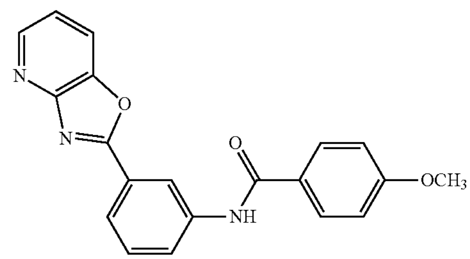 [SMILES: COc1ccc(C(=O)Nc2cccc(-c3nc4ncccc4o3)c2)cc1] |
| 17 | 22.15 | 6877227 | 355.4 | N,N-diethyl-2-[(8-methoxy-6-oxo-6H-benzo[c]chromen-3-yl)oxy]acetamide | 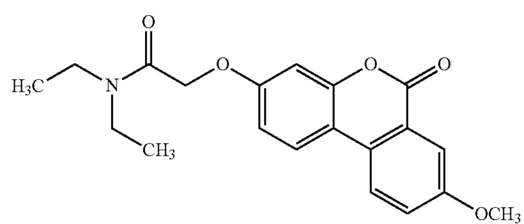 [SMILES: CCN(CC)C(=O)COc1ccc2c(c1)oc(=O)c1cc(OC)ccc12] |
| 18 | 21.82 | 6559548 | 282.7 | 2-[2-(2-chlorophenyl)vinyl]-4(3H)-quinazolinone | 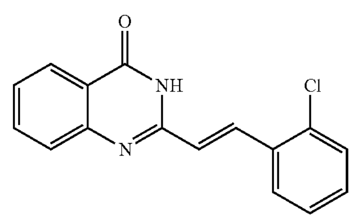 [SMILES: O=c1[nH]c(/C=C/c2ccccc2Cl)nc2ccccc12] |
| 19 | 21.24 | 9011680 | 355.8 | N-(4-chloro-3-[1,3]oxazolo[4,5-b]pyridin-2-ylphenyl)-2-thiophenecarboxamide | 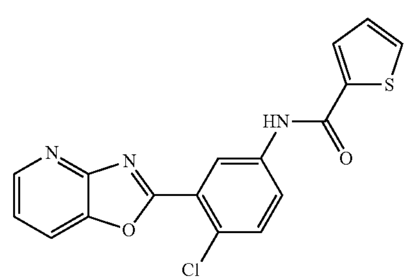 [SMILES: O=C(Nc1ccc(Cl)c(-c2nc3ncccc3o2)c1)c1cccs1] |
| 20 | 19.78 | 7657422 | 337.4 | 2-fluoro-N-(3-imidazo[2,1-b][1,3]thiazol-6-ylphenyl)benzamide | 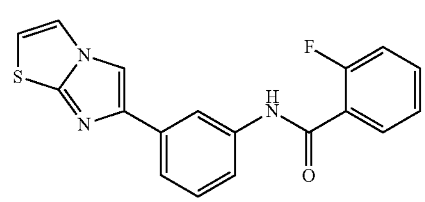 [SMILES: O=C(Nc1cccc(-c2cn3ccsc3n2)c1)c1ccccc1F] |

TABLE 2-continued

171 High Throughput Screen HITS

| Rank # | Avg Normalized % maximal activity | ChemBridge compound ID# | MW | Mol Name | Structure |
|---|---|---|---|---|---|
| 21 | 17.70 | 6879357 | 382.5 | 4-[4-(2-furoyl)-1-piperazinyl]-6-methyl-5,6,7,8-tetrahydro[1]benzothieno[2,3-d]pyrimidine | 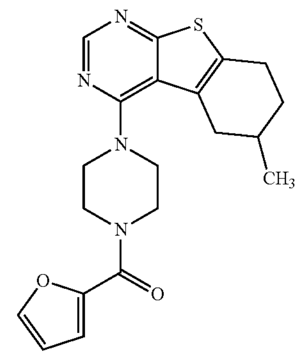 [SMILES: CC1CCc2sc3ncnc(N4CCN(C(=O)c5ccco5)CC4)c3c2C1] |
| 22 | 17.36 | 7946040 | 343.4 | N,N,4-trimethyl-2-{[(3-methyl-1-benzofuran-2-yl)carbonyl]amino}-1,3-thiazole-5-carboxamide | 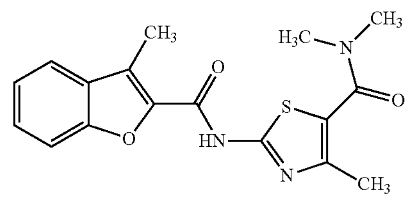 [SMILES: Cc1nc(NC(=O)c2oc3ccccc3c2C)sc1C(=O)N(C)C] |
| 23 | 16.77 | 7683456 | 284.3 | 5-(4-fluorophenyl)-7-(2-furyl)-4,5,6,7-tetrahydro[1,2,4]triazolo[1,5-a]pyrimidine | 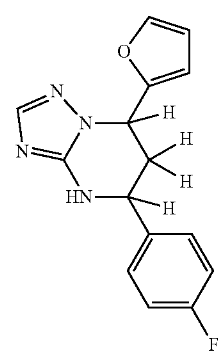 [SMILES: Fc1ccc(C2CC(c3ccco3)n3ncnc3N2)cc1] |
| 24 | 16.16 | 5968546 | 306.8 | 2-chloro-N-(7-oxo-4,5,6,7-tetrahydro-1,3-benzothiazol-2-yl)benzamide | 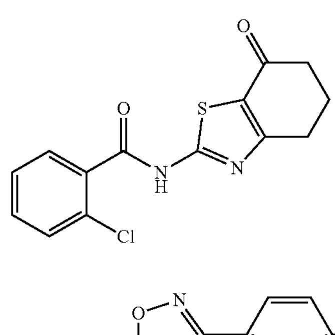 |
| 25 | 15.69 | 9006419 | 373.5 | 1-{4-[3-(4-ethoxy-3-methoxyphenyl)-1,2,4-oxadiazol-5-yl]butanoyl}piperidine | 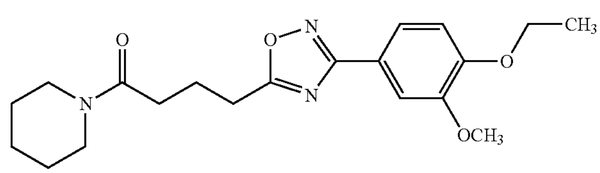 [SMILES: CCOc1ccc(-c2noc(CCCC(=O)N3CCCCC3)n2)cc1OC] |

TABLE 2-continued

171 High Throughput Screen HITS

| Rank # | Avg Normalized % maximal activity | ChemBridge compound ID# | MW | Mol Name | Structure |
|---|---|---|---|---|---|
| 26 | 15.22 | 9010523 | 325.3 | N-{4-[5-(2-furyl)-1,3,4-oxadiazol-2-yl]phenyl}tetrahydro-2-furancarboxamide | 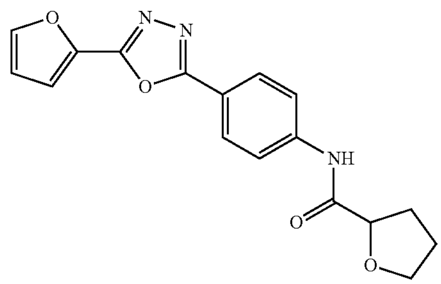 [SMILES: O=C(Nc1ccc(-c2nnc(-c3ccco3)o2)cc1)C1CCCO1] |
| 27 | 14.03 | 9064718 | 345.4 | N-[5-(1,3-benzoxazol-2-yl)-2-methoxyphenyl] nicotinamide | 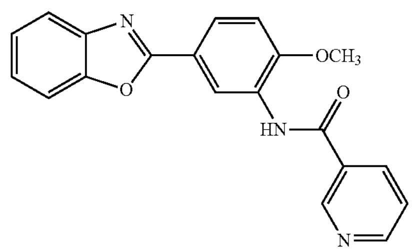 [SMILES: COc1ccc(-c2nc3ccccc3o2)cc1NC(=O)c1cccnc1] |
| 28 | 13.98 | 6553394 | 293.3 | 2-methyl-N-(4-methyl-2-oxo-2H-chromen-7-yl) benzamide | 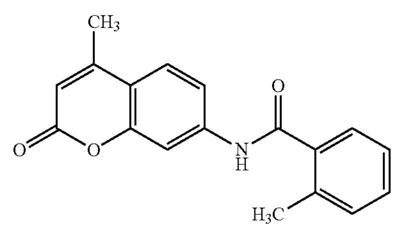 [SMILES: Cc1ccccc1C(=O)Nc1ccc2c(C)cc(=O)oc2c1] |
| 29 | 13.58 | 6038917 | 266.3 | 1-methoxy-4-(4-methoxyphenyl) phthalazine | 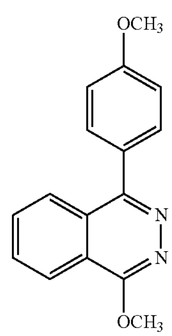 [SMILES: COc1ccc(-c2nnc(OC)c3ccccc23)cc1] |
| 30 | 13.43 | 6537559 | 331.3 | N-[4-(5-phenyl-1,3,4-oxadiazol-2-yl)phenyl]-2-furamide | 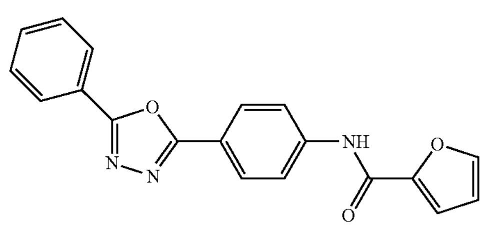 [SMILES: O=C(Nc1ccc(-c2nnc(-c3ccccc3)o2)cc1)c1ccco1] |

TABLE 2-continued

| 171 High Throughput Screen HITS | | | | | |
|---|---|---|---|---|---|
| Rank # | Avg Normalized % maximal activity | ChemBridge compound ID# | MW | Mol Name | Structure |
| 31 | 13.00 | 7928241 | 350 | N-(3-{[(2-ethoxyphenyl)amino]carbonyl}phenyl)-2-furamide | |
| 32 | 12.03 | 7993034 | 319.8 | N-(5-chloro-2-methoxyphenyl)-5-(2-pyrazinyl)-1,3,4-thiadiazol-2-amine | |
| 33 | 11.98 | 7959093 | 378.4 | methyl 2-{[3-(2-furoylamino)-2-methylbenzoyl]amino}benzoate | |
| 34 | 11.27 | 5705452 | 315.4 | 2-[2-(1,2-dimethyl-1H-indol-3-yl)vinyl]-4(3H)-quinazolinone | |
| 35 | 11.40 | 6564017 | 361.4 | N-{4-[5-(2-furyl)-1,3,4-oxadiazol-2-yl]phenyl}-3-methoxybenzamide | |

TABLE 2-continued

| 171 High Throughput Screen HITS | | | | | |
|---|---|---|---|---|---|
| Rank # | Avg Normalized % maximal activity | Chem-Bridge compound ID# | MW | Mol Name | Structure |
| 36 | 11.14 | 7798230 | 281.4 | N-(2-ethyl-6-methylphenyl)-2-thiophenesulfonamide | |
| 37 | 10.61 | 7994462 | 389.4 | 3,4-dimethoxy-N-(2-methyl-4-[1,3]oxazolo[4,5-b]pyridin-2-ylphenyl)benzamide | |
| 38 | 10.61 | 01504018 | 1221.407 | HEDERACOSIDE C | |
| 39 | 10.52 | 7962796 | 322.4 | N-[4-(5-methyl-1,3-benzoxazol-2-yl)phenyl]tetrahydro-2-furancarboxamide | |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 40 | 10.29 | 9028215 | 372.4 | ethyl 5-[(2-fluorobenzoyl)amino]-2-(4-morpholinyl)benzoate | 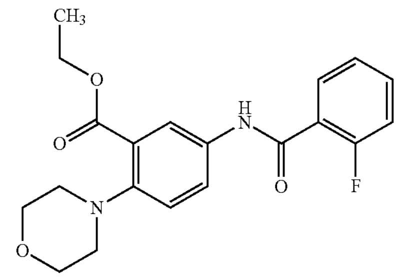 [SMILES: CCOC(=O)c1cc(NC(=O)c2ccccc2F)ccc1N1CCOCC1] |
| 41 | 10.28 | 9010768 | 319.3 | N-(2-methyl-4-[1,3]oxazolo[4,5-b]pyridin-2-ylphenyl)-2-furamide | 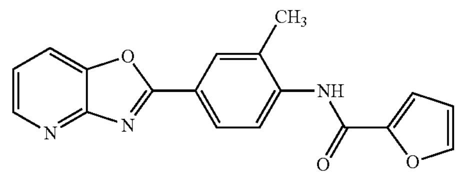 [SMILES: Cc1cc(-c2nc3ncccc3o2)ccc1NC(=O)c1ccco1] |
| 42 | 10.16 | 7893379 | 335.4 | N-[4-(5-phenyl-1,3,4-oxadiazol-2-yl)phenyl]tetrahydro-2-furancarboxamide | 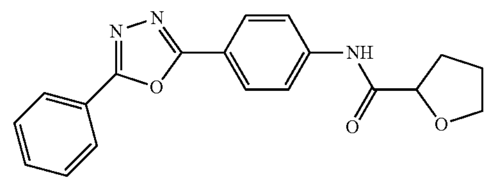 [SMILES: O=C(Nc1ccc(-c2nnc(-c3ccccc3)o2)cc1)C1CCCO1] |
| 43 | 9.52 | 9006085 | 327.3 | N-({[6-(4-morpholinyl)-4-pyrimidinyl]amino}carbonyl)benzamide | 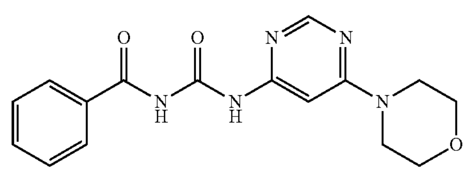 [SMILES: O=C(NC(=O)c1ccccc1)Nc1cc(N2CCOCC2)ncn1] |
| 44 | 9.07 | 7961939 | 345.4 | N-{4-[5-(2-furyl)-1,3,4-oxadiazol-2-yl]phenyl}-3-methylbenzamide | 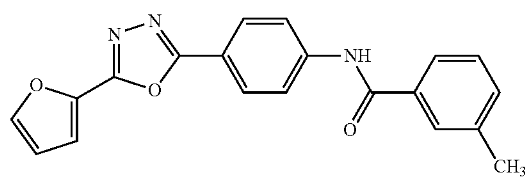 |
| 45 | 8.97 | 7985495 | 372.3 | 1-({[5-(2,4-dichlorophenyl)-1,3,4-oxadiazol-2-yl]thio}acetyl)piperidine | 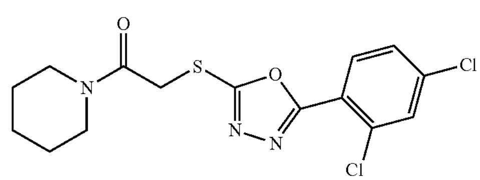 [SMILES: O=C(CSc1nnc(-c2ccc(Cl)cc2Cl)o1)N1CCCCC1] |
| 46 | 8.94 | 9048901 | 349.5 | 2-({[2-(1,3-benzodioxol-5-yl)-1,3-thiazol-4-yl]methyl}thio)-5-methyl-1,3,4-thiadiazole | 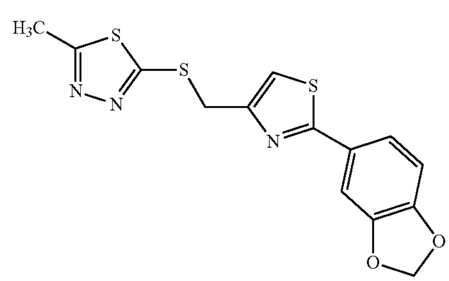 [SMILES: Cc1nnc(SCc2csc(-c3ccc4c(c3)OCO4)n2)s1] |

TABLE 2-continued

| 171 High Throughput Screen HITS | | | | | |
|---|---|---|---|---|---|
| Rank # | Avg Normalized % maximal activity | ChemBridge compound ID# | MW | Mol Name | Structure |
| 47 | 8.66 | 7747935 | 293.3 | N-[5-ethoxymethyl)-1,3,4-thiadiazol-2-yl]-4-methoxybenzamide | |
| 48 | 8.44 | 6817240 | 244.3 | N-[1-(4-ethylphenyl)ethyl]-1H-1,2,4-triazole-3-carboxamide | |
| 49 | 8.36 | 7496480 | 308.3 | N-[4-(1,3-benzoxazol-2-yl)phenyl]tetrahydro-2-furancarboxamide | |
| 50 | 8.23 | 6404083 | 355.5 | N-(4-ethoxyphenyl)-N-[2-(4-methyl-1-piperazinyl)-2-oxoethyl] methanesulfonamide (non-preferred name) | |
| 51 | 8.11 | 9039418 | 344.4 | ethyl 5-(2-furoylamino)-2-morpholin-4-ylbenzoate | |
| 52 | 8.03 | 7452875 | 340.4 | methyl 2-{[3-(isobutyrylamino) benzoyl]amino} benzoate | |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 53 | 7.94 | 7850005 | 357.4 | 3-amino-4-(methoxymethyl)-N-(3-methoxyphenyl)-6-methylthieno[2,3-b]pyridine-2-carboxamide | 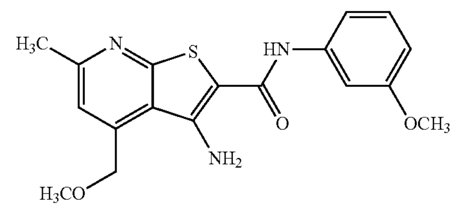 [SMILES: COCc1cc(C)nc2sc(C(=O)Nc3cccc(OC)c3)c(N)c12] |
| 54 | 7.83 | 9010110 | 345.4 | N-[2-methoxy-5-(2-quinoxalinyl)phenyl]-2-furamide | 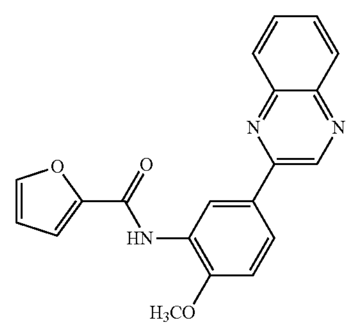 [SMILES: COc1ccc(-c2cnc3ccccc3n2)cc1NC(=O)c1ccco1] |
| 55 | 7.75 | 7959285 | 327.4 | N-cyclopentyl-9-methyl-4-oxo-4H-pyrido[1,2-a]thieno[2,3-d]pyrimidine-2-carboxamide | 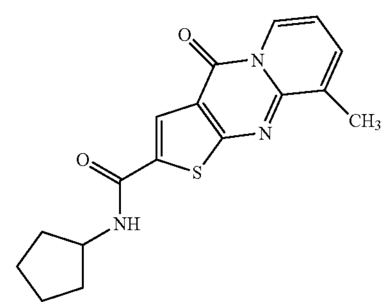 [SMILES: Cc1cccn2c(=O)c3cc(C(=O)NC4CCCC4)sc3nc12] |
| 56 | 7.69 | 7367373 | 352.4 | N-(2-fluorophenyl)-2-([1,2,4]triazolo[4,3-a]quinolin-1-ylthio)acetamide | 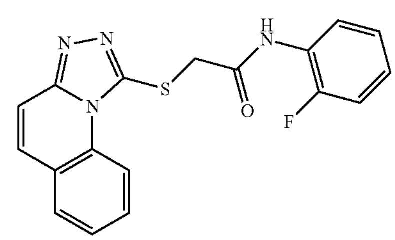 [SMILES: O=C(CSc1nnc2ccc3ccccc3n12)Nc1ccccc1F] |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 57 | 7.64 | 6522581 | 390.5 | N,N-diethyl-4-[4-(4-morpholinyl)-1-phthalazinyl]benzamide | 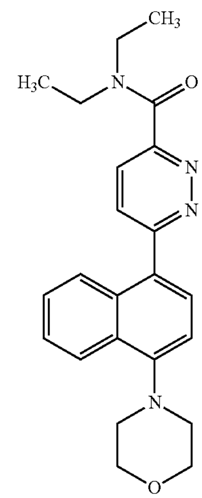 [SMILES: CCN(CC)C(=O)c1ccc(-c2ccc(N3CCOCC3)c3ccccc23)nn1] |
| 58 | 7.63 | 7937664 | 361.4 | N-[5-(1,3-benzothiazol-2-yl)-2-methoxyphenyl]nicotinamide | 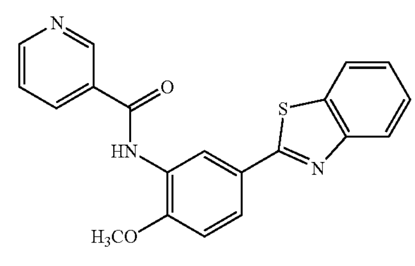 [SMILES: COc1ccc(-c2nc3ccccc3s2)cc1NC(=O)c1cccnc1] |
| 59 | 7.59 | 7760781 | 347.4 | 2-methyl-4-[4-(1-piperidinylcarbonyl)phenyl]-1(2H)-phthalazinone | 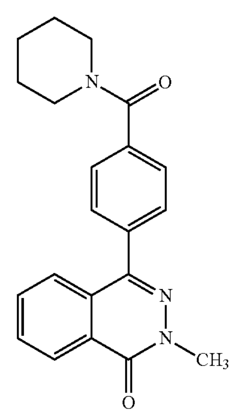 [SMILES: Cn1nc(-c2ccc(C(=O)N3CCCCC3)cc2)c2ccccc2c1=O] |

TABLE 2-continued

171 High Throughput Screen HITS

| Rank # | Avg Normalized % maximal activity | ChemBridge compound ID# | MW | Mol Name | Structure |
|---|---|---|---|---|---|
| 60 | 7.53 | 7239935 | 302.8 | 3-chloro-6-methyl-N-3-pyridinyl-1-benzothiophene-2-carboxamide | 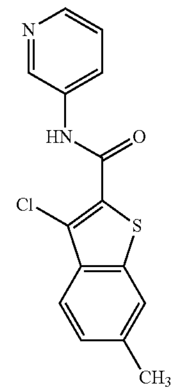 [SMILES: Cc1ccc2c(Cl)c(C(=O)Nc3cccnc3)sc2c1] |
| 61 | 7.27 | 7440531 | 318.4 | N-(5,5-dimethyl-7-oxo-4,5,6,7-tetrahydro-1,3-benzothiazol-2-yl)-2-fluorobenzamide | 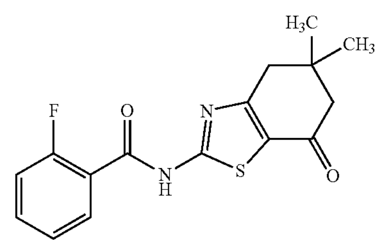 [SMILES: CC1(C)CC(=O)c2sc(NC(=O)c3ccccc3F)nc2C1] |
| 62 | 7.27 | 6766980 | 269.3 | 2-(1-naphthyl)-N-1,3,4-thiadiazol-2-ylacetamide | 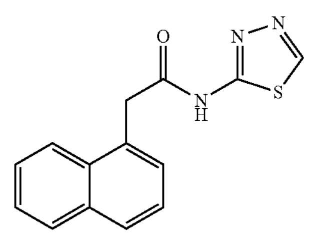 [SMILES: O=C(Cc1cccc2ccccc12)Nc1nncs1] |
| 63 | 7.19 | 7905968 | 315.4 | 2-[(2,5-dimethoxyphenyl)amino]-4H-pyrido[3,2-e][1,3]thiazin-4-one | 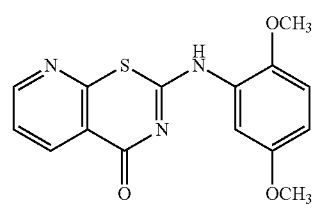 [SMILES: COc1ccc(OC)c(Nc2nc(=O)c3cccnc3s2)c1] |
| 64 | 7.14 | 7996110 | 373.5 | 1-{4-[3-(3-ethoxy-4-methoxyphenyl)-1,2,4-oxadiazol-5-yl]butanoyl}piperidine | 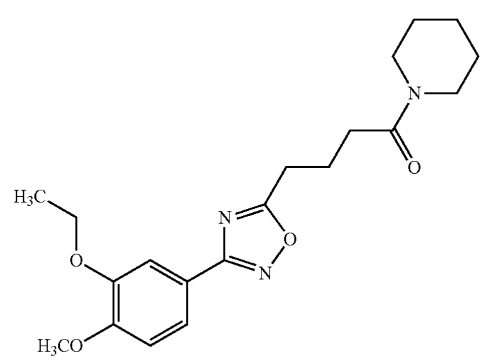 [SMILES: CCOc1cc(-c2noc(CCCC(=O)N3CCCCC3)n2)ccc1OC] |

TABLE 2-continued

171 High Throughput Screen HITS

| Rank # | Avg Normalized % maximal activity | ChemBridge compound ID# | MW | Mol Name | Structure |
|---|---|---|---|---|---|
| 65 | 7.09 | 7965947 | 321.3 | N-(3-{[(4-methyl-2-pyridinyl)amino]carbonyl}phenyl)-2-furamide | 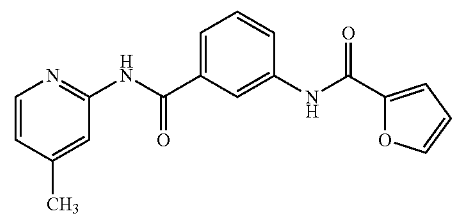 [SMILES: Cc1ccnc(NC(=O)c2cccc(NC(=O)c3ccco3)c2)c1] |
| 66 | 7.04 | 6412989 | 280.3 | 1-{5-[2-(1-methyl-1H-benzimidazol-2-yl)vinyl]-2-furyl}-1-propanone | 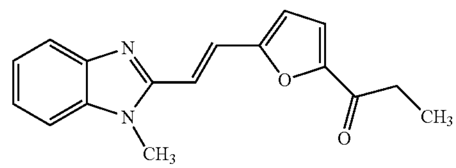 [SMILES: CCC(=O)c1ccc(/C=C/c2nc3ccccc3n2C)o1] |
| 67 | 6.98 | 7912790 | 377.4 | N-[2-methoxy-5-(2-oxo-2H-chromen-3-yl)phenyl]-2-thiophenecarboxamide | 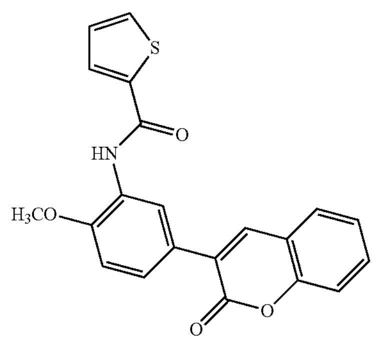 [SMILES: COc1ccc(-c2cc3ccccc3oc2=O)cc1NC(=O)c1cccs1] |
| 68 | 6.79 | 6040127 | 295.8 | N-(5-tert-butyl-1,3,4-thiadiazol-2-yl)-3-chlorobenzamide | 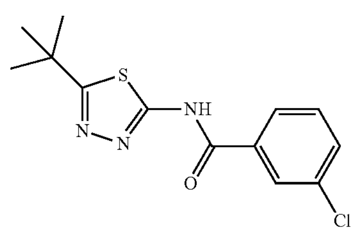 [SMILES: CC(C)(C)c1nnc(NC(=O)c2cccc(Cl)c2)s1] |
| 69 | 6.74 | 5977021 | 297.4 | 1-(2-methoxybenzyl)-4-(2-pyridinylmethyl)piperazine | 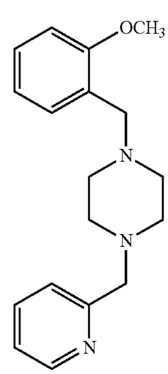 [SMILES: COc1ccccc1CN1CCN(Cc2ccccn2)CC1] |

TABLE 2-continued

171 High Throughput Screen HITS

| Rank # | Avg Normalized % maximal activity | ChemBridge compound ID# | MW | Mol Name | Structure |
|---|---|---|---|---|---|
| 70 | 6.71 | 7948013 | 376.4 | 2-oxo-N-[4-(1-piperidinylcarbonyl)phenyl]-2H-chromene-3-carboxamide | 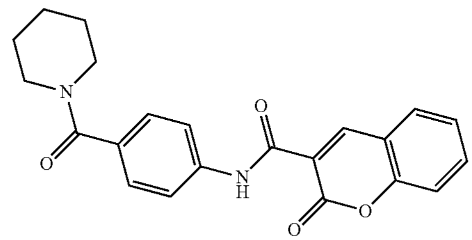 [SMILES: O=C(Nc1ccc(C(=O)N2CCCCC2)cc1)c1cc2ccccc2oc1=O] |
| 71 | 6.67 | 6013429 | 350.4 | 2-[4-oxo-4-(1-piperidinyl)butyl]-1H-benzo[de]isoquinoline-1,3(2H)-dione | 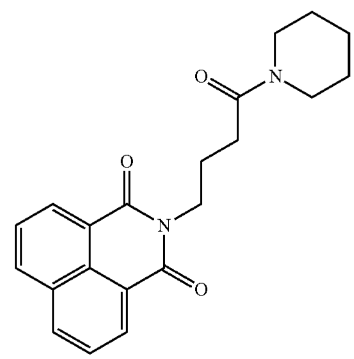 [SMILES: O=C(CCCN1C(=O)c2cccc3cccc(c23)C1=O)N1CCCCC1] |
| 72 | 6.56 | 01500872 | 387.8 | PALMATINE CHLORIDE | 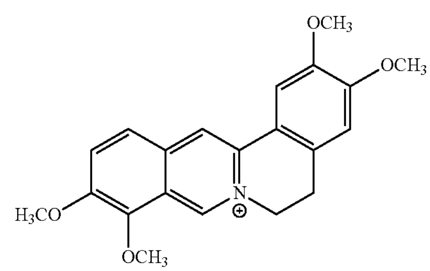 [SMILES: COc1cc2c(cc1OC)-c1cc3ccc(OC)c(OC)c3c[n+]1CC2] |
| 73 | 6.43 | 9038800 | 380.4 | methyl 5-[(1-benzofuran-2-ylcarbonyl)amino]-2-morpholin-4-ylbenzoate | 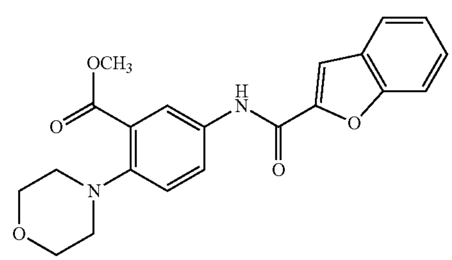 [SMILES: COC(=O)c1cc(NC(=O)c2cc3ccccc3o2)ccc1N1CCOCC1] |
| 74 | 6.35 | 01500439 | 298.4 | NORETHYNODREL | 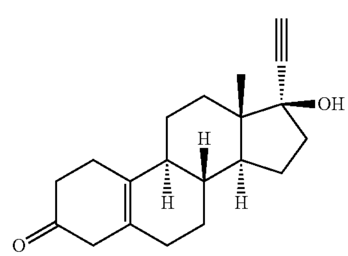 |

TABLE 2-continued

| 171 High Throughput Screen HITS |||||||
|---|---|---|---|---|---|
| Rank # | Avg Normalized % maximal activity | Chem-Bridge compound ID# | MW | Mol Name | Structure |
| 75 | 6.27 | 7794138 | 334.4 | N-{3-[(3,5-dimethylbenzoyl)amino]phenyl}-2-furamide | |
| 76 | 6.23 | 6738335 | 385 | N-{3-[(3-bromobenzoyl)amino]phenyl}-2-furamide | |
| 77 | 6.18 | 01500308 | 244.2681 | FLURBIPROFEN | |
| 78 | 6.16 | 7367458 | 325.3 | N-(4-methoxyphenyl)-2-[(2-oxo-2H-chromen-7-yl)oxy]acetamide | |
| 79 | 6.01 | 7903471 | 366.2 | ethyl 4-{[(4-bromo-1-ethyl-1H-pyrazol-3-yl)carbonyl]amino}benzoate | |
| 80 | 5.99 | 7967399 | 395.8 | 5-chloro-N-{3-[5-(2-furyl)-1,3,4-oxadiazol-2-yl]phenyl}-2-methoxybenzamide | |
| 81 | 5.81 | 00300548 | 332.4 | SPARTEINE SULFATE | |

TABLE 2-continued

171 High Throughput Screen HITS

| Rank # | Avg Normalized % maximal activity | ChemBridge compound ID# | MW | Mol Name | Structure |
|---|---|---|---|---|---|
| 82 | 5.76 | 01500213 | 279.1 | CYCLOPHOSPHAMIDE HYDRATE | 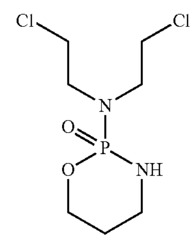 [SMILES: O=P1(N(CCCl)CCCl)NCCCO1] |
| 83 | 5.75 | 7288111 | 333.4 | 2-[(2-ethoxybenzoyl)amino]-N,N,4-trimethyl-1,3-thiazole-5-carboxamide | 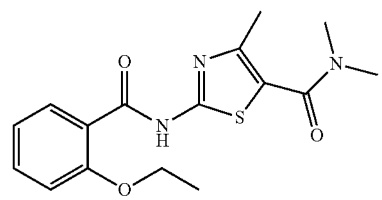 [SMILES: CCOc1ccccc1C(=O)Nc1nc(C)c(C(=O)N(C)C)s1] |
| 84 | 5.72 | 01500450 | 205.6 | OXIDOPAMINE HYDROCHLORIDE | 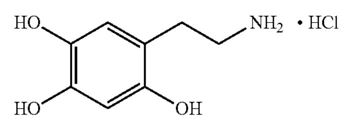 [SMILES: "· HCl" ; NCCc1cc(O)c(O)cc1O] |
| 85 | 5.64 | 6021809 | 384.2 | 5-bromo-N-[2-(3-pyridinyl)-1,3-benzoxazol-5-yl]-2-furamide | 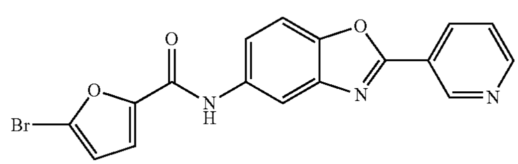 [SMILES: O=C(Nc1ccc2oc(-c3cccnc3)nc2c1)c1ccc(Br)o1] |
| 86 | 5.63 | 7414973 | 322.4 | 4-methyl-N-[4-(1-piperidinylcarbonyl)phenyl]benzamide | 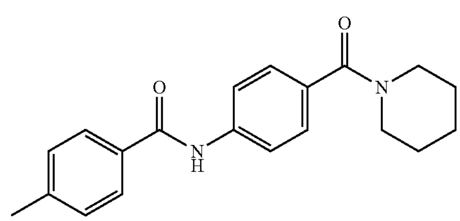 [SMILES: Cc1ccc(C(=O)Nc2ccc(C(=O)N3CCCCC3)cc2)cc1] |
| 87 | 5.62 | 7975466 | 313.7 | N-(5-chloro-2-methoxyphenyl)-6-quinoxaline-carboxamide | 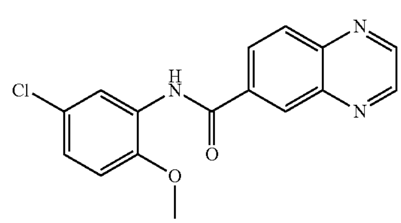 [SMILES: COc1ccc(Cl)cc1NC(=O)c1ccc2nccnc2c1] |
| 88 | 5.42 | 7035480 | 353.4 | N-(4-methoxyphenyl)-2-[(4-methyl-2-oxo-2H-chromen-6-yl)oxy]propanamide | 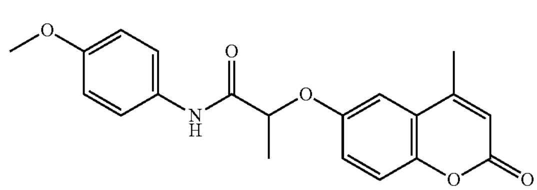 [SMILES: COc1ccc(NC(=O)C(C)Oc2ccc3oc(=O)cc(C)c3c2)cc1] |

TABLE 2-continued

171 High Throughput Screen HITS

| Rank # | Avg Normal- ized % maximal activity | Chem- Bridge com- pound ID# | MW | Mol Name | Structure |
|---|---|---|---|---|---|
| 89 | 5.35 | 9008857 | 359.4 | 3-methoxy-N-(2-methyl-4-[1,3]oxazolo[4,5-b]pyridin-2-ylphenyl)benzamide | 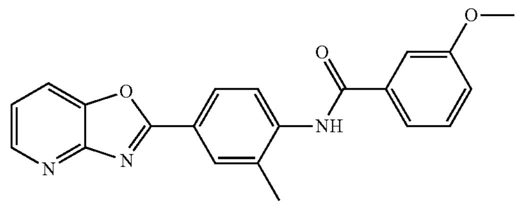 [SMILES: COc1cccc(C(=O)Nc2ccc(-c3nc4ncccc4o3)cc2C)c1] |
| 90 | 5.22 | 7849244 | 311.4 | 2-(methylthio)-N-(4-oxo-1,4-dihydro-2-quinazolinyl)benzamide | 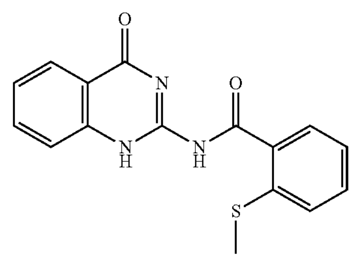 [SMILES: CSc1ccccc1C(=O)Nc1nc(=O)c2ccccc2[nH]1] |
| 91 | 5.19 | 7991640 | 351.8 | ethyl 4-({[5-chloro-2-(methylthio)-4-pyrimidinyl]carbonyl}amino)benzoate | 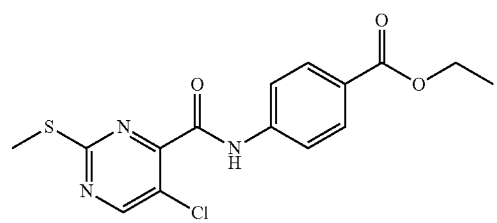 [SMILES: CCOC(=O)c1ccc(NC(=O)c2nc(SC)ncc2Cl)cc1] |
| 92 | 5.16 | 9009463 | 361.4 | N-(2-methoxy-5-(2-quinoxalinyl)phenyl]-2-thiophenecarboxamide | 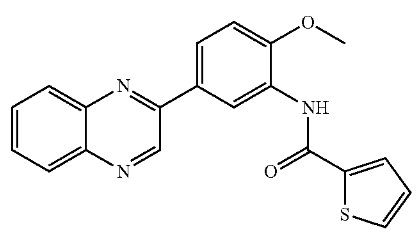 [SMILES: COc1ccc(-c2cnc3ccccc3n2)cc1NC(=O)c1cccs1] |
| 93 | 5.16 | 01503267 | 354.4 | NOMIFENSINE MALEATE | 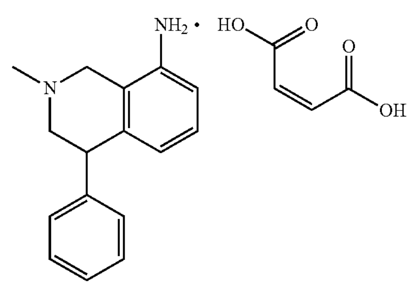 |
| 94 | 5.01 | 6081762 | 247.3 | 3,5-dimethyl-N-(5-methyl-1,3,4-thiadiazol-2-yl)benzamide | 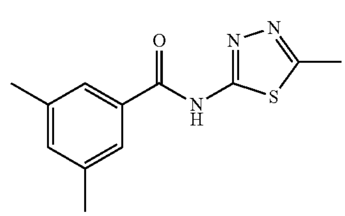 |

TABLE 2-continued

| | | | | | |
|---|---|---|---|---|---|
| | 171 High Throughput Screen HITS | | | | |
| Rank # | Avg Normalized % maximal activity | ChemBridge compound ID# | MW | Mol Name | Structure |
| 95 | 5.00 | 01504079 | 994.1 | TOMATINE | |
| 96 | 4.92 | 6695225 | 333 | 2-fluoro-N-(3-[1,3]oxazolo[4,5-b]pyridin-2-ylphenyl)benzamide | |
| 97 | 4.86 | 9064465 | 237.6 | 3-(4-chlorophenyl)-N-methyl-1,2,4-oxadiazole-5-carboxamide | |
| 98 | 4.84 | 01504173 | 345.7 | FLUOXETINE | |

TABLE 2-continued

171 High Throughput Screen HITS

| Rank # | Avg Normalized % maximal activity | ChemBridge compound ID# | MW | Mol Name | Structure |
|---|---|---|---|---|---|
| 99 | 4.83 | 7888484 | 368.4 | methyl 2-({4-[(tetrahydro-2-furanylcarbonyl)amino]benzoyl}amino)benzoate | 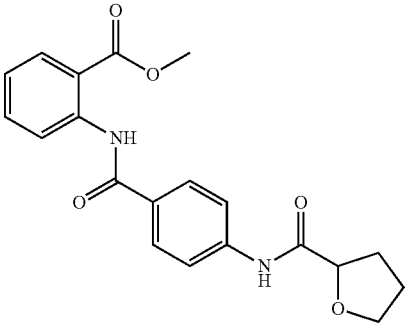 [SMILES: COC(=O)c1ccccc1NC(=O)c1ccc(NC(=O)C2CCCO2)cc1] |
| 100 | 4.83 | 7988613 | 347.3 | 5-cyclopropyl-N-3-pyridinyl-7-(trifluoromethyl)pyrazolo[1,5-a]pyrimidine-2-carboxamide | 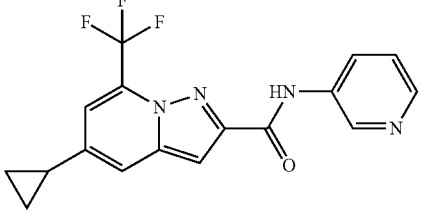 |
| 101 | 4.78 | 5360051 | 338.2 | 3-bromo-N-(2,6-dimethoxy-4-pyrimidinyl)benzamide | 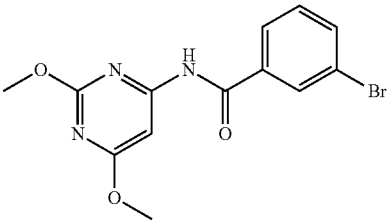 [SMILES: COc1cc(NC(=O)c2cccc(Br)c2)nc(OC)n1] |
| 102 | 4.76 | 01503092 | 178.1 | GLUCONOLACTONE | 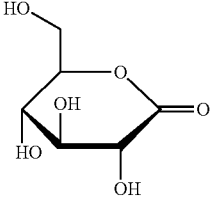 |
| 103 | 4.74 | 9011206 | 337.8 | N-[5-(1H-benzimidazol-2-yl)-2-chlorophenyl]-2-furamide | 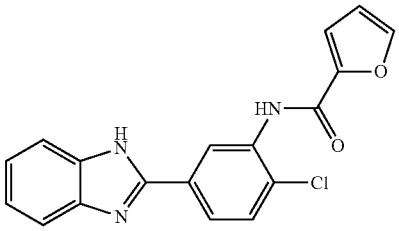 [SMILES: O=C(Nc1cc(-c2nc3ccccc3[nH]2)ccc1Cl)c1ccco1] |
| 104 | 4.72 | 7588223 | 272.3 | 3-(cyclopentylamino)-1-(3-methylphenyl)-2,5-pyrrolidinedione | 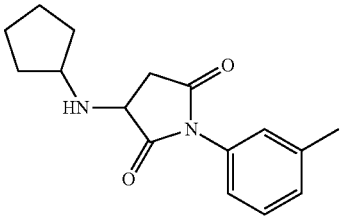 [SMILES: Cc1cccc(N2C(=O)CC(NC3CCCC3)C2=O)c1] |

TABLE 2-continued

171 High Throughput Screen HITS

| Rank # | Avg Normalized % maximal activity | ChemBridge compound ID# | MW | Mol Name | Structure |
|---|---|---|---|---|---|
| 105 | 4.70 | 6725477 | 329.4 | 2-methyl-N-(4-[1,3]oxazolo[4,5-b]pyridin-2-ylphenyl)benzamide | 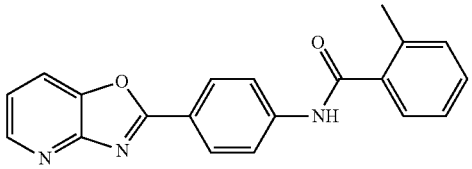 [SMILES: Cc1ccccc1C(=O)Nc1ccc(-c2nc3ncccc3o2)cc1] |
| 106 | 4.69 | 7650421 | 297.3 | N-(4-methoxyphenyl)-1-oxo-3,4-dihydro-1H-isochromene-3-carboxamide | 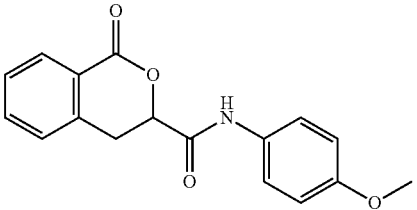 [SMILES: COc1ccc(NC(=O)C2Cc3ccccc3C(=O)O2)cc1] |
| 107 | 4.67 | 6233363 | 398.9 | N~1~-(4-chlorophenyl)-N~2~-(2,4-dimethoxyphenyl)-N~2~-(methylsulfonyl)glycinamide | 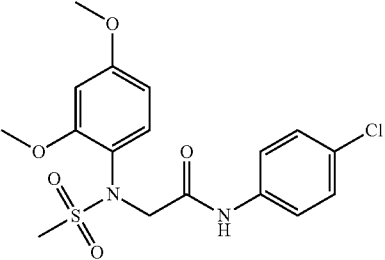 [SMILES: COc1ccc(N(CC(=O)Nc2ccc(Cl)cc2)S(C)(=O)=O)c(OC)c1] |
| 108 | 4.66 | 6955524 | 363.5 | 3-amino-N-(5-ethyl-1,3,4-thiadiazol-2-yl)-4-(methoxymethyl)-6-methylthieno[2,3-b]pyridine-2-carboxamide | 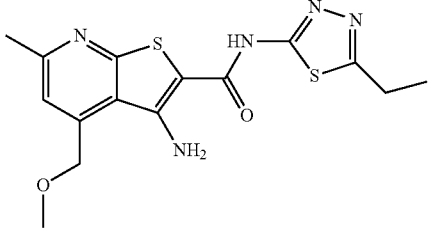 [SMILES: CCc1nnc(NC(=O)c2sc3nc(C)cc(COC)c3c2N)s1] |
| 109 | 4.65 | 01300029 | 195.2 | MEGLUMINE | 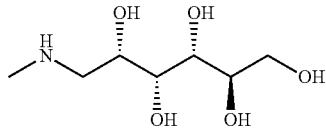 |
| 110 | 4.61 | 9025773 | 337.4 | N-{4-[5-(2-furyl)-1,3,4-oxadiazol-2-yl]phenyl}cyclohexanecarboxamide | 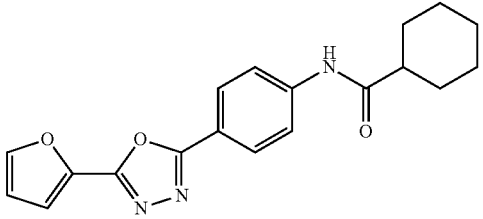 [SMILES: O=C(Nc1ccc(-c2nnc(-c3ccco3)o2)cc1)C1CCCCC1] |
| 111 | 4.58 | 7013997 | 355.4 | [2-(4-tert-butyl-2-methylphenoxy)ethyl](2-methoxyethyl)amine oxalate | 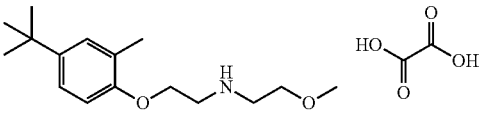 [SMILES: COCCNCCOc1ccc(C(C)(C)C)cc1C ; O=C(O)C(=O)O] |

TABLE 2-continued

171 High Throughput Screen HITS

| Rank # | Avg Normalized % maximal activity | ChemBridge compound ID# | MW | Mol Name | Structure |
|---|---|---|---|---|---|
| 112 | 4.55 | 7956221 | 394.4 | methyl 2-({2-methyl-3-[(2-thienylcarbonyl)amino]benzoyl}amino)benzoate | 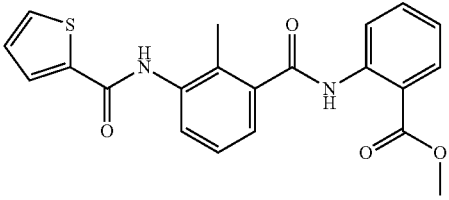 [SMILES: COC(=O)c1ccccc1NC(=O)c1cccc(NC(=O)c2cccs2)c1C] |
| 113 | 4.39 | 5576336 | 295.4 | N-[5-(ethylthio)-1,3,4-thiadiazol-2-yl]-3-methoxybenzamide | 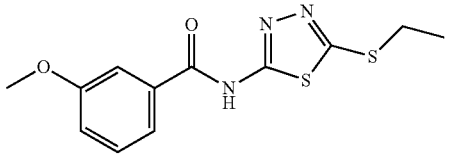 [SMILES: CCSc1nnc(NC(=O)c2cccc(OC)c2)s1] |
| 114 | 4.37 | 9010207 | 307.4 | N-{3-[5-(2-methylphenyl)-1,3,4-oxadiazol-2-yl]phenyl}propanamide | 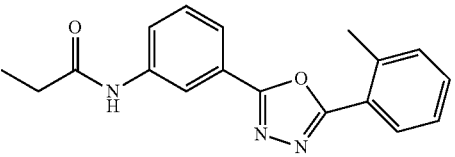 [SMILES: CCC(=O)Nc1cccc(-c2nnc(-c3ccccc3C)o2)c1] |
| 115 | 4.36 | 6430817 | 275.4 | N-(3,4-dimethylphenyl)-2-[(1-methyl-1H-imidazol-2-yl)thio]acetamide | 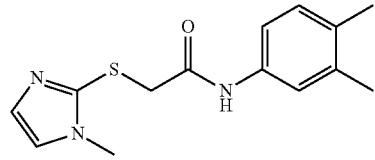 [SMILES: Cc1ccc(NC(=O)CSc2nccn2C)cc1C] |
| 116 | 4.34 | 6719009 | 362.4 | N-{3-[(2-thienylcarbonyl)amino]phenyl}-1-benzofuran-2-carboxamide | 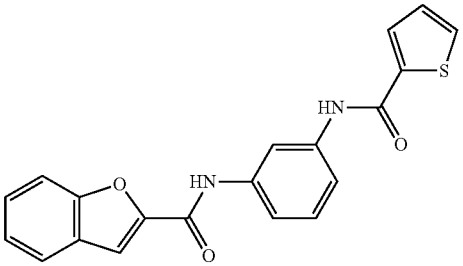 [SMILES: O=C(Nc1cccc(NC(=O)c2cccs2)c1)c1cc2ccccc2o1] |
| 117 | 4.28 | 9053934 | 353.8 | N-(4-chloro-2,5-dimethoxyphenyl)-2-[(4-methyl-2-pyrimidinyl)thio]acetamide | 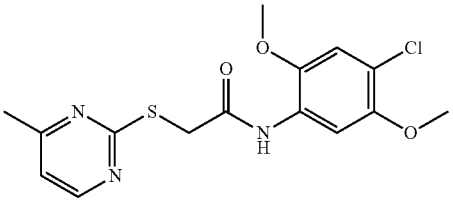 |
| 118 | 4.28 | 5140897 | 175.2 | 1-phenyl-1H-1,2,4-triazole-3,5-diamine | 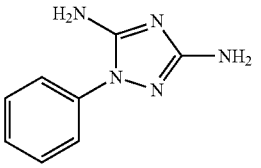 [SMILES: Nc1nc(N)n(-c2ccccc2)n1] |

TABLE 2-continued

| 171 High Throughput Screen HITS | | | | | |
|---|---|---|---|---|---|
| Rank # | Avg Normal- ized % maximal activity | Chem- Bridge com- pound ID# | MW | Mol Name | Structure |
| 119 | 4.25 | 7746407 | 385.4 | methyl 4-({[3-amino-4-(methoxymethyl)-6-methylthieno[2,3-b]pyridin-2-yl]carbonyl}amino)benzoate | |
| 120 | 4.25 | 01505715 | 241.2 | PANTOTHENIC ACID(d) Na salt | |
| 121 | 4.13 | 01500380 | 344.4 | MEDRYSONE | |
| 122 | 4.13 | 9016281 | 373.4 | 2-methoxy-3-methyl-N-(2-methyl-5-[1,3]oxazolo[4,5-b]pyridin-2-ylphenyl)benzamide | |
| 123 | 4.10 | 7240114 | 373.2 | 3-iodo-N-(5-isopropyl-1,3,4-thiadiazol-2-yl)benzamide | |
| 124 | 3.95 | 7815100 | 389.9 | 4-(5-chloro-2-methylphenyl)-N-(2,5-dimethoxyphenyl)-1-piperazine-carboxamide | |

TABLE 2-continued

171 High Throughput Screen HITS

| Rank # | Avg Normalized % maximal activity | ChemBridge compound ID# | MW | Mol Name | Structure |
|---|---|---|---|---|---|
| 125 | 3.89 | 7947685 | 379 | 5-bromo-2-chloro-N-[5-(ethylthio)-1,3,4-thiadiazol-2-yl]benzamide | 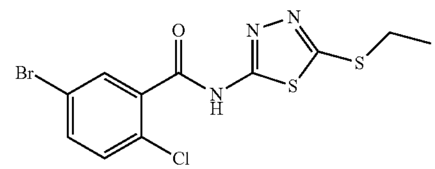 [SMILES: CCSc1nnc(NC(=O)c2cc(Br)ccc2Cl)s1] |
| 126 | 3.87 | 5932561 | 295.4 | N-(4-methoxyphenyl)-1-phenylcyclopentane-carboxamide | 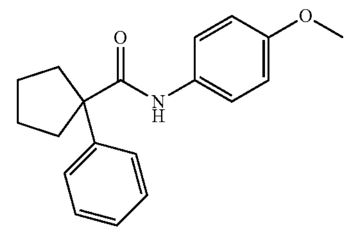 [SMILES: COc1ccc(NC(=O)C2(c3ccccc3)CCCC2)cc1] |
| 127 | 3.85 | 01504567 | 433.5 | MYCOPHENOLATE MOFETIL | 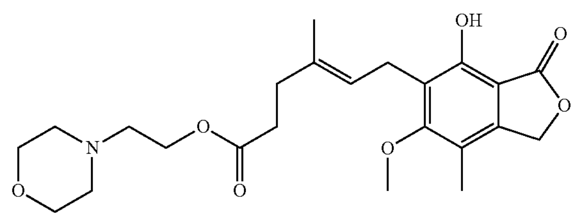 [SMILES: COc1c(C)c2c(c(O)c1C/C=C(\C)CCC(=O)OCCN1CCOCC1)C(=O)OC2] |
| 128 | 3.74 | 7999638 | 339.4 | 2-[2-(3,4-dimethoxyphenyl)vinyl]-5-(1-piperidinyl)-1,3-oxazole-4-carbonitrile | 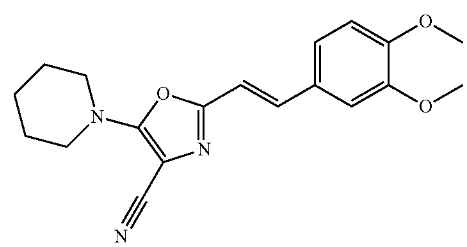 [SMILES: COc1ccc(/C=C/c2nc(C#N)c(N3CCCCC3)o2)cc1OC] |
| 129 | 3.73 | 00300564 | 154.2 | MENTHONE | 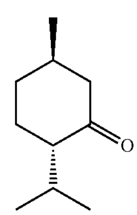 |
| 130 | 3.69 | 6159633 | 273.4 | 1-(cyclohexylcarbonyl)-4-(2-pyridinyl)piperazine | 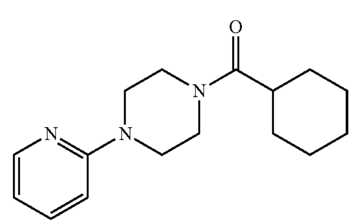 [SMILES: O=C(C1CCCCC1)N1CCN(c2ccccn2)CC1] |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 131 | 3.65 | 6943365 | 324.4 | 5-(diethylsulfonio)-1-(4-fluorobenzyl)-2,6-dioxo-1,2,3,6-tetrahydro-4-pyrimidinolate | 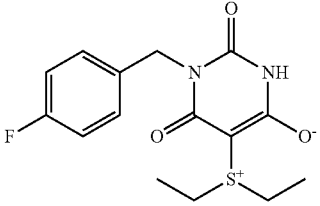 [SMILES: CC[S+](CC)c1c([O-])[nH]c(=O)n(Cc2ccc(F)cc2)c1=O] |
| 132 | 3.60 | 7887983 | 375.8 | 2-chloro-N-[4-(5-phenyl-1,3,4-oxadiazol-2-yl)phenyl]benzarnide | 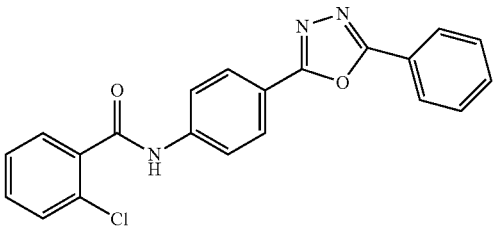 [SMILES: O=C(Nc1ccc(-c2nnc(-c3ccccc3)o2)cc1)c1ccccc1Cl] |
| 133 | 3.57 | 7682260 | 335.4 | 5-(4-methoxyphenyl)-7-(2-methylphenyl)-4,5,6,7-tetrahydro[1,2,4]triazolo[1,5-a]pyrimidin-2-amine | 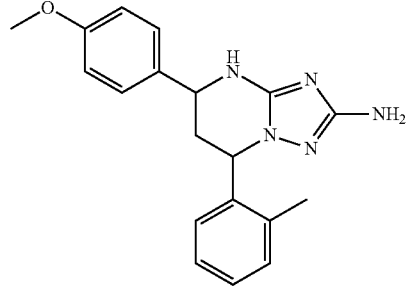 [SMILES: COc1ccc(C2CC(c3ccccc3C)n3nc(N)nc3N2)cc1] |
| 134 | 3.56 | 9025775 | 310.3 | 7-(1,3-benzodioxol-5-ylmethoxy)-4-methyl-2H-chromen-2-one | 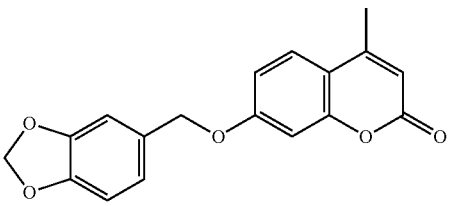 [SMILES: Cc1cc(=O)oc2cc(OCc3ccc4c(c3)OCO4)ccc12] |
| 135 | 3.47 | 01500401 | 398.3 | METHSCOPOLAMINE BROMIDE | 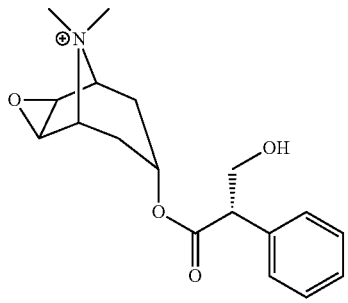 [SMILES: C[N+]1(C)C2CC(OC(=O)[C@H](CO)c3ccccc3)CC1C1OC12] |
| 136 | 3.43 | 9038064 | 361.5 | 4-+(1,6-dimethyl-3,4-dihydropyrrolo[1,2-a]pyrazin-2(1H)-yl)carbonyl]-N,N-dimethyl-benzenesulfonamide | 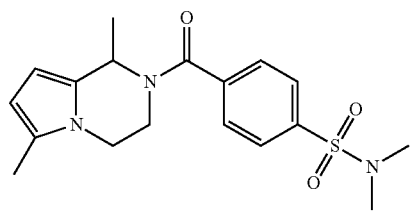 [SMILES: Cc1ccc2n1CCN(C(=O)c1ccc(S(=O)(=O)N(C)C)cc1)C2C] |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 137 | 3.37 | 6778405 | 391.2 | 5-bromo-N-{3-[(2-thienylcarbonyl)amino]phenyl}-2-furamide | 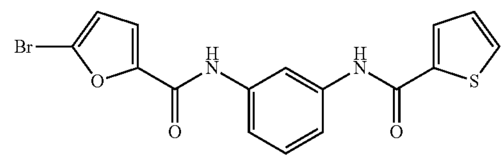 [SMILES: O=C(Nc1cccc(NC(=O)c2cccs2)c1)c1ccc(Br)o1] |
| 138 | 3.31 | 7953705 | 397.4 | 3,4,5-trimethoxy-N-[4-(2-thienylcarbonyl)phenyl]benzamide | 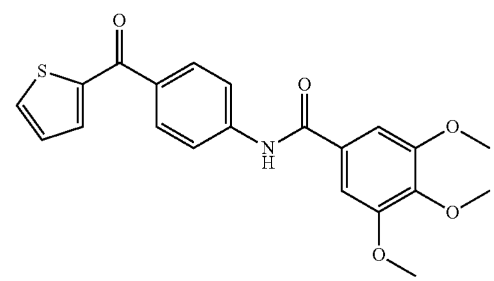 [SMILES: COc1cc(C(=O)Nc2ccc(C(=O)c3cccs3)cc2)cc(OC)c1OC] |
| 139 | 3.27 | 7946783 | 287 | N-(4,6-dimethyl-2-pyrimidinyl)-4,5,6,7-tetrahydro-1-benzothiophene-2-carboxamide | 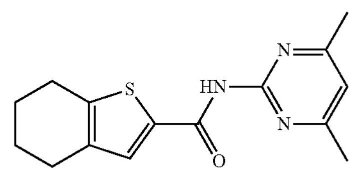 [SMILES: Cc1cc(C)nc(NC(=O)c2cc3c(s2)CCCC3)n1] |
| 140 | 3.21 | 6080049 | 218.3 | 7-ethoxy-4,8-dimethyl-2H-chromen-2-one | 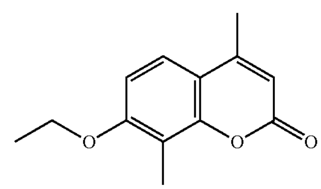 [SMILES: CCOc1ccc2c(C)cc(=O)oc2c1C] |
| 141 | 3.21 | 9017829 | 360.4 | 2-{[(4-methyl-6-phenyl-2-pyrimidinyl)thio]methyl}-4(3H)-quinazolinone | 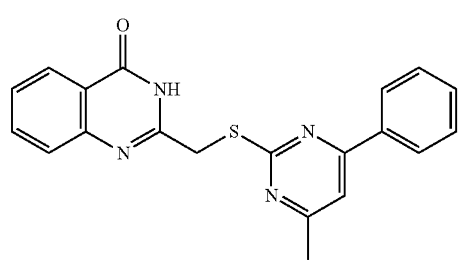 [SMILES: Cc1cc(-c2ccccc2)nc(SCc2nc3ccccc3c(=O)[nH]2)n1] |
| 142 | 3.09 | 9035014 | 349.4 | 2-(3,4-dimethoxyphenyl)-5-{[(2-methyl-1,3-thiazol-4-yl)methyl]thio}-1,3,4-oxadiazole | 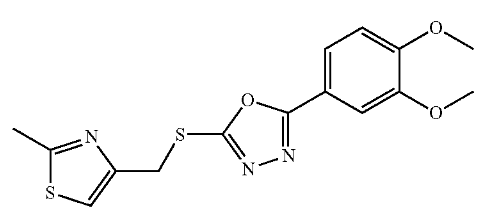 |
| 143 | 3.07 | 5920020 | 391.5 | N-(4-acetylphenyl)-2-[(5-methyl-5H-[1,2,4]triazino[5,6-b]indol-3-yl)thio]acetamide | 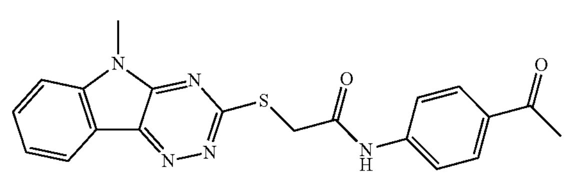 [SMILES: CC(=O)c1ccc(NC(=O)CSc2nnc3c4ccccc4n(C)c3n2)cc1] |

TABLE 2-continued

171 High Throughput Screen HITS

| Rank # | Avg Normalized % maximal activity | ChemBridge compound ID# | MW | Mol Name | Structure |
|---|---|---|---|---|---|
| 144 | 3.04 | 5967862 | 309.4 | 5,6-dimethyl-2-[(4,6,7-trimethyl-2-quinazolinyl)amino]-4(1H)-pyrimidinone | 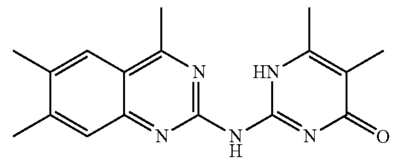 [SMILES: Cc1cc2nc(Nc3nc(=O)c(C)c(C)[nH]3)nc(C)c2cc1C] |
| 145 | 3.02 | 6698327 | 373.4 | N-(3-[1,3]oxazolo[4,5-b]pyridin-2-ylphenyl)-2,3-dihydro-1,4-benzodioxine-6-carboxamide | 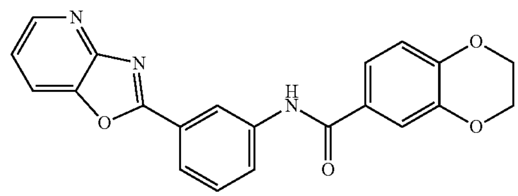 [SMILES: O=C(Nc1cccc(-c2nc3ncccc3o2)c1)c1ccc2c(c1)OCCO2] |
| 146 | 2.97 | 5932619 | 349.3 | 4-methyl-N-[4-(3-pyridinyl)-1,3-thiazol-2-yl]-2-pyridinamine hydrobromide | 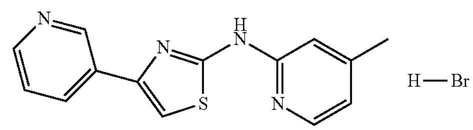 |
| 147 | 2.77 | 6303674 | 339 | N-(4-acetylphenyl)-2-[(5-methyl-1H-benzimidazol-2-yl)thio]acetamide | 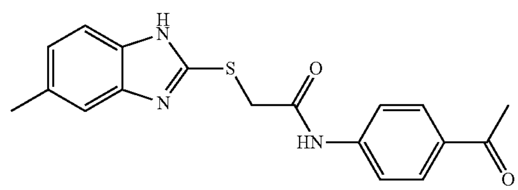 [SMILES: CC(=O)c1ccc(NC(=O)CSc2nc3cc(C)ccc3[nH]2)cc1] |
| 148 | 2.74 | 5150578 | 368.5 | N-{3-[(cyclohexylamino)methyl]-4,5,6,7-tetrahydro-1-benzothien-2-yl}benzamide | 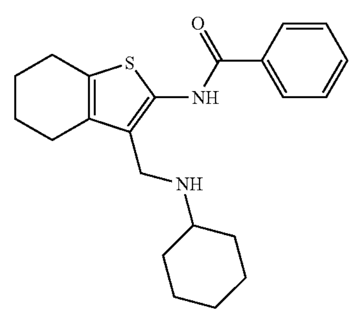 [SMILES: O=C(Nc1sc2c(c1CNC1CCCCC1)CCCC2)c1ccccc1] |
| 149 | 2.71 | 6097291 | 335.4 | N-[3-(3,4-dimethylbenzoyl)phenyl]-2-thiophenecarboxamide | 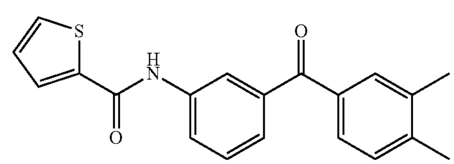 [SMILES: Cc1ccc(C(=O)c2cccc(NC(=O)c3cccs3)c2)cc1C] |
| 150 | 2.62 | 7982108 | 383.2 | N-(2-bromophenyl)-3-methyl-2-oxo-2,3-dihydro-1,3-benzoxazole-6-sulfonamide | 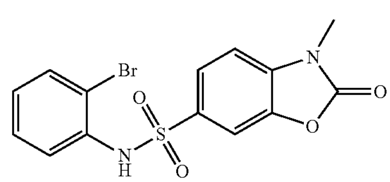 [SMILES: Cn1c(=O)oc2cc(S(=O)(=O)Nc3ccccc3Br)ccc21] |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 151 | 2.60 | 01500324 | 270.0 | HALAZONE | 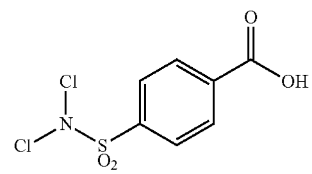 [SMILES: O=C(O)c1ccc(S(=O)(=O)N(Cl)Cl)cc1] |
| 152 | 2.56 | 5847086 | 276.7 | 5-chloro-2-methoxy-N-(4-methyl-2-pyridinyl)benzamide | 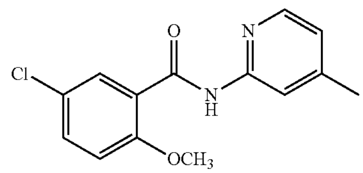 [SMILES: COc1ccc(Cl)cc1C(=O)Nc1cc(C)ccn1] |
| 153 | 2.37 | 9037834 | 338.4 | N-cyclohexyl-N,1-dimethyl-4-oxo-1,4-dihydropyrido[1,2-a]pyrrolo[2,3-d]pyrimidine-2-carboxamide | 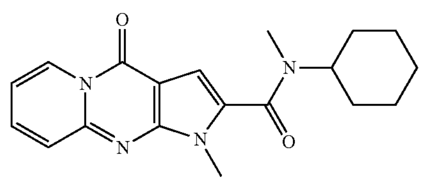 [SMILES: CN(C(=O)c1cc2c(=O)n3ccccc3nc2n1C)C1CCCCC1] |
| 154 | 2.30 | 6985863 | 386.4 | N-(2,4-dimethoxyphenyl)-1-(4-fluorobenzoyl)-4-piperidinecarboxamide | 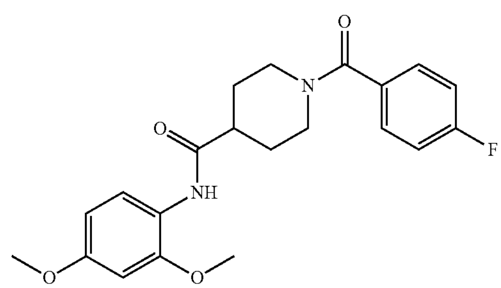 [SMILES: COc1ccc(NC(=O)C2CCN(C(=O)c3ccc(F)cc3)CC2)c(OC)c1] |
| 155 | 2.20 | 7925769 | 359 | 4-[(4-methyl-1-piperazinyl)sulfonyl]-N-phenylbenzamide | 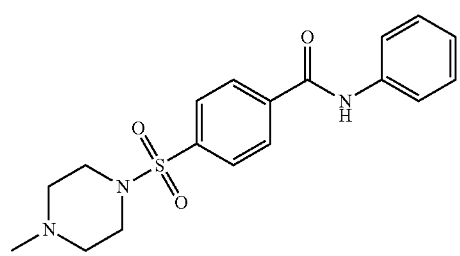 [SMILES: CN1CCN(S(=O)(=O)c2ccc(C(=O)Nc3ccccc3)cc2)CC1] |
| 156 | 2.17 | 7254774 | 332.4 | N-[3-methoxy-4-(pentanoylamino)phenyl]-2-thiophenecarboxamide | 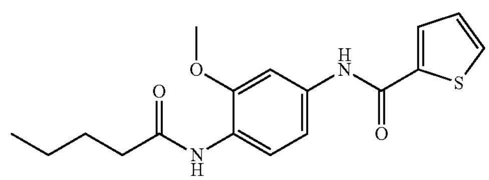 [SMILES: CCCCC(=O)Nc1ccc(NC(=O)c2cccs2)cc1OC] |
| 157 | 2.12 | 9001373 | 312.4 | N-(2,4-dimethylphenyl)-2-(3H-imidazo[4,5-b]pyridin-2-ylthio)acetamide | 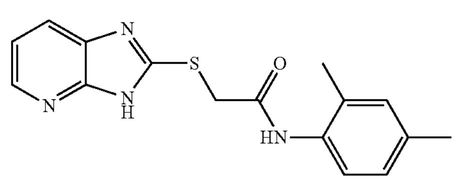 [SMILES: Cc1ccc(NC(=O)CSc2nc3cccnc3[nH]2)c(C)c1] |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 158 | 2.12 | 6039445 | 355.4 | 2-methoxy-N-{5-[(4-methylphenoxy)methyl]-1,3,4-thiadiazol-2-yl}benzamide | 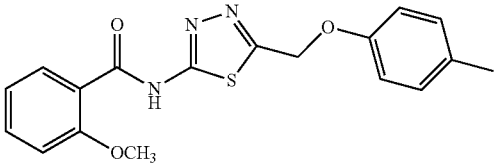 [SMILES: COc1ccccc1C(=O)Nc1nnc(COc2ccc(C)cc2)s1] |
| 159 | 2.12 | 6207364 | 259.3 | N-(3-methoxyphenyl)-N-(methylsulfonyl)glycine | 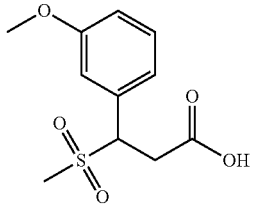 [SMILES: COc1cccc(C(CC(=O)O)S(C)(=O)=O)c1] |
| 160 | 2.09 | 6317347 | 363.5 | 2-{[6-(acetylamine)-1,3-benzothiazol-2-yl]thio)-N-cyclohexylacetamide | 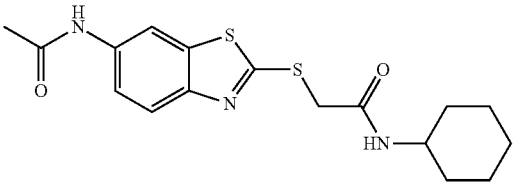 [SMILES: CC(=O)Nc1ccc2nc(SCC(=O)NC3CCCCC3)sc2c1] |
| 161 | 2.08 | 5921934 | 316.4 | ethyl [(5-ethyl-5H-[1,2,4]triazino[5,6-b]indol-3-yl)thio]acetate | 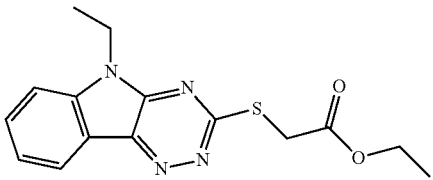 [SMILES: CCOC(=O)CSc1nnc2c3ccccc3n(CC)c2n1] |
| 162 | 2.04 | 7878578 | 384.5 | N-[4-(acetylamino)phenyl]-3-amino-4-(methoxymethyl)-6-methylthieno[2,3-b]pyridine-2-carboxamide | 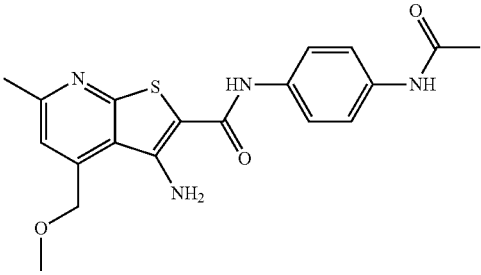 [SMILES: COCc1cc(C)nc2sc(C(=O)Nc3ccc(NC(C)=O)cc3)c(N)c12] |
| 163 | 2.04 | 5942394 | 337.4 | N-(2,5-dimethoxyphenyl)-2-(2-naphthyloxy)acetamide | 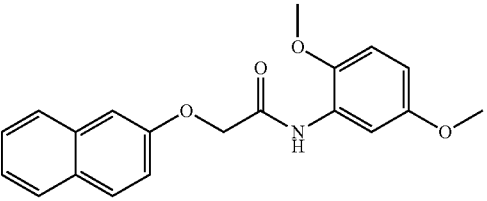 [SMILES: COc1ccc(OC)c(NC(=O)COc2ccc3ccccc3c2)c1] |

TABLE 2-continued

171 High Throughput Screen HITS

| Rank # | Avg Normalized % maximal activity | Chem-Bridge compound ID# | MW | Mol Name | Structure |
|---|---|---|---|---|---|
| 164 | 2.01 | 6835420 | 310.3 | 6-fluoro-4-(4-nitrophenyl)-3a,4,5,9b-tetrahydro-3H-cyclopenta[c]quinoline | 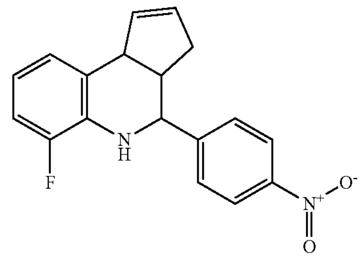 [SMILES: O=[N+]([O-])c1ccc(C2Nc3c(F)cccc3C3C=CCC32)cc1] |
| 165 | 2.01 | 7949438 | 259.4 | 2-phenyl-N-(2-thienylmethyl)butanamide | 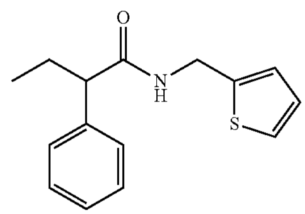 [SMILES: CCC(C(=O)NCc1cccs1)c1ccccc1] |
| 166 | 1.98 | 7999574 | 397.4 | 3,11-bis(2-furylmethyl)-3,11-dihydro-4H-pyrimido[5',4',4,5]pyrrolo[2,3-b]quinoxalin-4-one | 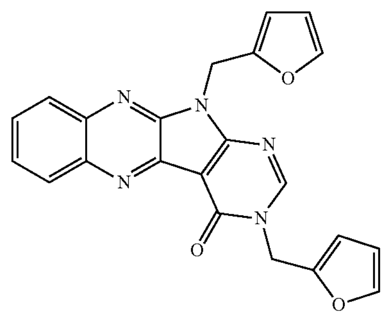 [SMILES: O=c1c2c3nc4ccccc4nc3n(Cc3ccco3)c2ncn1Cc1ccco1] |
| 167 | 1.96 | 5143670 | 347.8 | N-(6-chloro-2-phenylimidazo[1,2-a]pyridin-3-yl)benzamide | 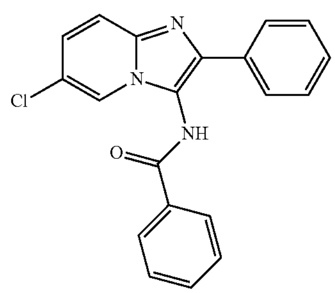 [SMILES: O=C(Nc1c(-c2ccccc2)nc2ccc(Cl)cn12)c1ccccc1] |
| 168 | 1.93 | 6303049 | 357.5 | N-[4-(acetylamino)phenyl]-2-(1,3-benzothiazol-2-ylthio)acetamide | 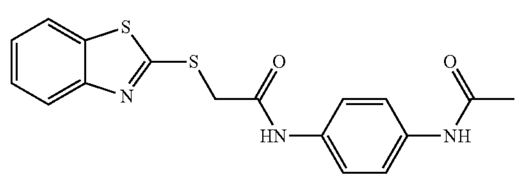 [SMILES: CC(=O)Nc1ccc(NC(=O)CSc2nc3ccccc3s2)cc1] |
| 169 | 1.85 | 5859874 | 245.3 | N-(4-fluorophenyl)-N'-(5-methyl-2-pyridinyl)urea | 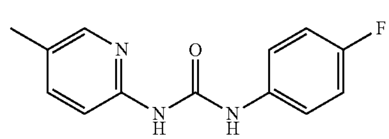 [SMILES: Cc1ccc(NC(=O)Nc2ccc(F)cc2)nc1] |

TABLE 2-continued

171 High Throughput Screen HITS

| Rank # | Avg Normalized % maximal activity | ChemBridge compound ID# | MW | Mol Name | Structure |
|---|---|---|---|---|---|
| 170 | 1.74 | 5834944 | 386.4 | 10-(1-pyrrolidinyl-carbonyl)-7-(trifluoromethyl)-5,6-dihydrobenzo[h]pyrazolo[5,1-b]quinazoline | 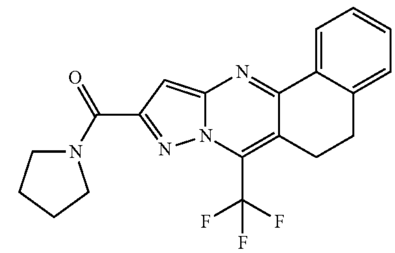 [SMILES: O=C(c1cc2nc3c(c(C(F)(F)F)n2n1)CCc1ccccc1-3)N1CCCC1] |
| 171 | 1.60 | 7649211 | 369.4 | N-(2,5-dimethoxyphenyl)-2-(6,7-dimethyl-3-oxo-1,2,3,4-tetrahydro-2-quinoxalinyl)acetamide | 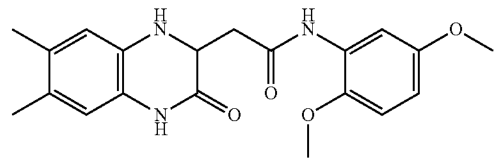 |

In certain embodiments, the invention relates to a pharmaceutical composition comprising a) pharmaceutically effective amount of a compound of Formula I, II or III, Table 1 or Table 2, or a pharmaceutically acceptable salt, solvate, poly-morph, tautomer or prodrug thereof. In certain embodiments, the compound further comprises a pharmaceutically acceptable carrier, diluent, excipient and/or adjuvant.

In yet additional embodiments, the invention relates to a method of treating, preventing, or inhibiting a parasitic auxotrophic infection in a patient, comprising administering a pharmaceutically effective amount of a compound of Formula I, II or III, Table 1 or Table 2.

Also provided is a method for inhibiting an equilibrative nucleoside transporter (ENT) of a Plasmodium species comprising contacting the Plasmodium species with a compound having a structure set forth herein, or a pharmaceutically acceptable salt or stereoisomer of any thereof or a physiological functional derivative of any thereof, in an amount effective to inhibit an ENT of a Plasmodium species.

In an embodiment, "patient" or "subject" refers to mammals and includes human and veterinary subjects, including avians. In an embodiment, the subject is mammalian.

In an embodiment the parasite is a Plasmodium species. In an embodiment, the parasite is a Plasmodium falciparum, P. berghei, P. vivax, P. ovale, P. malariae or P. knowlesi, a Leshmania species or Trypanasoma species. In a preferred embodiment, the parasite is Plasmodium falciparum.

In an embodiment, the parasite is a purine auxotroph.

In an embodiment, the compound is administered in a composition comprising a pharmaceutically acceptable carrier.

In an embodiment, the subject has an extant parasite infection and the method is for treating the parasite infection.

In certain embodiments, the invention relates to a method of the treatment or prophylaxis disorder or disease mediated by infection with a parasitic purine auxotroph, comprising administering to a patient in need thereof a therapeutically effective amount of the compound of Formula I, II or III, Table 1 or Table 2, or the pharmaceutical composition thereof. In an embodiment, the subject is at risk for a parasite infection and the method is for preventing (i.e., prophylaxis) or inhibiting parasite infection. Being at risk for a parasite infection is a term understood in the art, for example, wherein the subject is present in a geographic location in which said parasite is endemic. In an embodiment, the subject has cerebral malaria and the method includes treating cerebral malaria.

Also provided is a method for inhibiting an equilibrative nucleoside transporter (ENT) of a Plasmodium species comprising contacting the Plasmodium species with a compound having a structure set forth herein, or a pharmaceutically acceptable salt or stereoisomer of any thereof or a physiological functional derivative of any thereof, in an amount effective to inhibit an ENT of a Plasmodium species.

In an embodiment, the ENT is an ENT1, ENT2, ENT3 or ENT4. In an embodiment, the ENT is an ENT1. In an embodiment, the ENT is a P. falciparum ENT1.

In an embodiment, the parasite is a P. falciparum, P. berghei, P. vivax, P. ovale, P. malariae or P. knowlesi. In an embodiment, the parasite is a Plasmodium falciparum. In an embodiment, the compound is 2-(1-methyl-1H-indol-3-yl)-2-oxo-N-[4-(pyrrolidin-1-ylcarbonyl)phenyl]acetamide or N-(4-chloro-3-[1,3]oxazolo[4,5-b]pyridin-2-ylphenyl)-2-thiophenecarboxamide.

In an embodiment, the compounds or compositions comprising such are administered to a subject with an extant parasite infection. In an embodiment, the compounds or compositions comprising such are administered to a subject prophylactically. In an embodiment, the subject is at risk of the parasite infection, for example, the subject is present in, or will be present in, a geographic location where malaria is endemic.

In an embodiment, the ENT is a Plasmodium falciparum ENT type 1.

The compounds used in the methods of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

When the structure of the compounds used in this invention includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "*Enantiomers, Racemates and Resolutions*" by J. Jacques, A. Collet and S. Wilen, Pub. John Wiley & Sons, NY, 1981. For example, the resolution may be carried out by preparative chromatography on a chiral column.

The subject invention is also intended to include use of all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include carbon-13 and carbon-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

The compounds of the instant invention may be in a salt form. As used herein, a "salt" is salt of the instant compounds which has been modified by making acid or base, salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "alkyl" includes both branched and straight-chain saturated aliphatic hydrocarbon groups having the specified number of carbon atoms and may be unsubstituted or substituted. The Alkyls are C1-C10 alkyls, or a subset or individual thereof. In a non-limiting example, where the alkyl is C1-C5 as in "C1-C5 alkyl", it is defined to include groups having 1, 2, 3, 4 or 5 carbons in a linear or branched arrangement and specifically includes methyl, ethyl, n-propyl, isopropyl, n-butyl, t-butyl, and pentyl. Alkyl may optionally be substituted with phenyl or substituted phenyl to provide substituted or unsubstituted benzyl.

Heterocyclyl means a saturated or partially unsaturated monocyclic radical containing 3 to 8 ring atoms and preferably 5 to 6 ring atoms selected from carbon or nitrogen but not limited to pyrrolidine.

As used herein the term "aryl" refers to aromatic monocyclic or multicyclic groups containing from 5 to 15 carbon atoms. Aryl groups include, but are not limited to groups such as unsubstituted or substituted phenyl. When referring to said aryl being substituted, said substitution may be at any position on the ring, other than the point of attachment to the other ring system of a compound of the invention. Therefore, any hydrogen atom on the aryl ring may be substituted with a substituent defined by the invention. In embodiments where the aryl is a phenyl ring, said substitution may be at the meta- and/or ortho- and/or para-position relative to the point of attachment. Aryl may optionally be substituted with a heterocyclyl-C(O)— moiety which includes a pyrrolidinyl-C(O)— moiety.

The term "heteroaryl" as used herein, represents a stable monocyclic, bicyclic or polycyclic ring of up to 10 atoms in each ring, wherein at least one ring is aromatic and contains from 1 to 4 heteroatoms or particularly 1 to 2 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom. selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyriinidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is nonaromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

In the compounds of the present invention, the alkyl, aryl, or heteroaryl groups can be further substituted by replacing one or more hydrogen atoms be alternative non-hydrogen groups. These include, but are not limited to, 1-4 groups selected from alkyl, alkoxy, halo, hydroxy, mercapto, amino, carboxy, cyano and carbamoyl.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon (s) or hydrogen (s) atom are replaced by one or more bonds, including double or triple bonds, to a heteroatom. Examples of substituent groups include the functional groups described above, and, in particular, halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; heterocyclyl-C(O)-moiety; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity. Moreover, where hydrogens are not shown in the carbon-based structures herein, implicit hydrogens are understood to complete valences as required.

The compounds of the instant invention may be in a salt form. As used herein, a "salt" is salt of the instant compounds which has been modified by making acid or base, salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

Where a numerical range is provided herein for any parameter, it is understood that all numerical subsets of that numerical range, and all the individual integer values contained therein, are provided as part of the invention. Thus, C1-C10 alkyl includes the subset of alkyls which are 1-3 carbon atoms, the subset of alkyls which are 2-5 carbon atoms etc. as well as an alkyl which has 1 carbon atom, an alkyl which has 3 carbon atoms, an alkyl which has 10 carbon atom, etc.

In an embodiment, the purines discussed herein are one or more of adenosine, inosine, hypoxanthine, or adenine. In an embodiment, "determining" as used herein means experimentally determining.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

As used herein, "a compound of the invention" means a compound of formula I, II, or III) or Tables 1-2 or a salt, solvate or physiologically functional derivative thereof.

As used herein, the term "solvate" refers to a complex of variable stoichiometry formed by a solute (in this invention, a compound of formula I, II, or III or Tables 1-2, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g., a drug precursor) that is transformed in vive to yield a compound of formula (I, II, or III) or Tables 1-2, or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

All combinations of the various elements described herein are within the scope of the invention unless otherwise indicated herein or otherwise clearly contradicted by context. Whilst the embodiments for each variable have generally been listed above separately for each variable, this invention also includes those compounds in which several or each embodiment for compounds of formula (I, II, or III) or Tables 1-2 is selected from each of the embodiments listed above. Therefore, this invention is intended to include all combinations of embodiments for each variable.

The compounds of formula (I, II, or III) or Tables 1-2 and salts, solvates and physiologically functional derivatives thereof are believed to be inhibitors of Plasmodium falciparum Equilibrative Nucleoside Transporter Type I (PfENT1), and thus be potentially useful in the prevention or treatment of diseases, disorders and conditions associated with infections by parasites that are purine auxotrophs, those which are unable to perform de novo purine biosynthesis.

Examples of such parasitic purine auxotrophs include Plasmodium species that cause malaria, Leishmania species that cause leishmaniasis, Trypanosoma species that cause African sleeping sickness and Chagas disease and Toxoplasma species that cause toxoplasmosis.

The compound of formula (I, II, or III) or Tables 1-2 or its pharmaceutically acceptable salts and pharmaceutical compositions can be used to treat or prevent a variety of conditions or diseases mediated by infection with one or more parasitic purine auxotrophs. Such conditions and diseases include, but are not limited to: (1) malaria, including cerebral malaria; (2) leishmaniasis; (3) African sleeping sickness; (4) Chagas disease; and (5) toxoplasmosis.

The invention thus provides compounds of formula (I, II, or III) or Tables 1-2 and salts, solvates and physiologically functional derivatives thereof for use in therapy, and particularly in the treatment of diseases and conditions mediated by exposure or infection with one or more parasitic purine auxotrophs.

In a further embodiment, the present invention is directed to methods of regulating, modulating, or inhibiting Plasmodium falciparum Equilibrative Nucleoside Transporter Type I for the prevention and/or treatment of disorders related to infection with one or more parasitic purine auxotrophs.

In a further embodiment, the present invention provides a method of treatment of a patient suffering from a disorder mediated by infection with one or more parasitic purine auxotrophs, which comprises administering to said patient an effective amount of a compound of formula (I, II, or III) or Tables 1-2 or a pharmaceutically acceptable salt, solvate, or a physiologically functional derivative thereof.

In a further embodiment, the present invention provides for the use of a compound of formula (I, II, or III) or Tables 1-2, or a pharmaceutically acceptable salt or solvate thereof, or a physiologically functional derivative thereof, in the preparation of a medicament for the treatment of a disorder mediated by infection with one or more parasitic purine auxotrophs.

In a further embodiment said disorder is malaria. In a further embodiment said disorder is leishmaniasis. In yet another embodiment, said disorder is African sleeping sickness.

While it is possible that, for use in therapy, a compound of formula (I, II, or III) or Tables 1-2, as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of formula (I, II, or III) or Tables 1-2 and salts, solvates and physiological functional derivatives thereof, and one or more pharmaceutically acceptable carriers, diluents, or excipients. The compounds of formula (I, II, or III) or Tables 1-2 and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of formula (I, II, or II) or Tables 1-2, or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of formula (I, II, or III) or Tables 1-2, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), inhaled, nasal, ocular, or parenteral (including intravenous and intramuscular) route. Such compositions may be prepared by any method known in the art of pharmacy, for example by bringing into association the active ingredient with the carrier(s) or excipient(s).

In a further embodiment, the present invention provides a pharmaceutical composition adapted for administration by the oral route, the treatment of diseases and conditions related to infection with one of more parasitic protozoa Plasmodia, *Leishmania, Trypanosoma, Entamoeba, Giardia, Naegleria*, or *Trichomonas*.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including for example, the age and weight of the animal, the precise condition requiring treatment and its severity, the nature of the formulation, and the route of administration, and will ultimately be at the discretion of the attendant physician or veterinarian However, an effective amount of a compound of formula (I, II, or III) or Tables 1-2 for the treatment of diseases or conditions associated with parasitic auxotrophic infections, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of formula (I, II, or III) or Tables 1-2, per se.

Compounds of the present invention, and their salts and solvates, and physiologically functional derivatives thereof, may be employed alone or in combination with other therapeutic agents for the treatment of diseases and conditions related to infection with one of more of *Plasmodium, Leishmania, Trypanosoma, Entamoeba, Giardia, Naegleria*, and *Trichomonas* protozoa. Combination therapies according to the present invention thus comprise the administration of at least one compound of formula (I, II, or III) or Tables 1-2, or a pharmaceutically acceptable salt or solvate thereof, or a physiologically functional derivative thereof, and the use of at least one other pharmaceutically active agent. The compound(s) of compound of formula (I, II, or III) or Tables 1-2 and the other pharmaceutically active agent(s) may be administered together or separately and, when administered separately this may occur simultaneously or sequentially in any order. The amounts of the compound(s) of formula (I, II, or III) or Tables 1-2 and the other pharmaceutically active agent(s) and the relative timings of administration will be selected in order to achieve the desired combined therapeutic effect.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of the present invention may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of the present invention. Those skilled in the art will recognize if a stereocenter exists in compounds of the present invention. Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

Molecular Biology

In accordance with the present invention, there may be numerous tools and techniques within the skill of the art, such as those commonly used in molecular immunology, cellular immunology, pharmacology, and microbiology. See, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

"Treating" or "treatment" of a state, disorder or condition includes:

(1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

The benefit to a subject to be treated is either statistically significant or at least perceptible to the patient or to the physician.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

"Patient" or "subject" refers to mammals and includes human and veterinary subjects. Certain veterinary subjects may include avian species.

This invention will be better understood from the Experimental Details, which follow. However, one skilled in the art will readily appreciate that the specific methods and results discussed are merely illustrative of the invention as described more fully in the claims that follow thereafter.

DESCRIPTION OF PREFERRED EMBODIMENTS

The compounds described in this invention may be prepared from: (1) commercially available starting materials (2)

known starting materials which may be prepared as described in literature procedures or (3) experimental procedures herein.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps which may also require additional consideration as to the need to protect reactive functional groups to prevent undesired side reactions.

Figure 2:
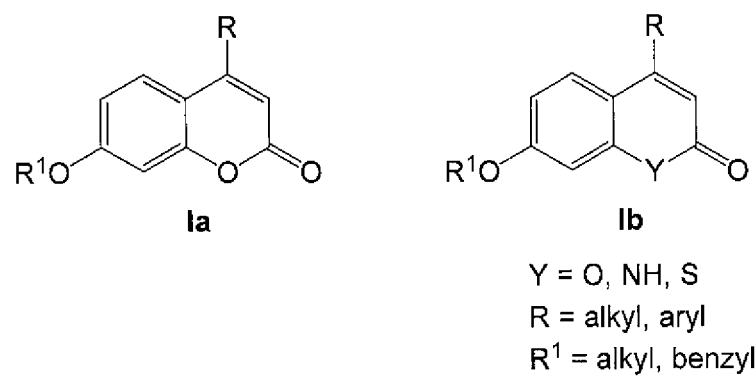
FIG. 2: General structure of the coumarin analogs.

Coumarins with general structure I (FIG. 2) are prepared according to the synthetic route reported by Lévai & Jekö (2005) presented in Scheme 1 wherein commercially available 7-hydroxy-4-methylcoumarin (1, R=CH$_3$) is alkylated with an alkyl halide R$^1$X in the presence of potassium iodide and potassium carbonate in an inert solvent which includes acetone to yield a coumarin with general structure I.

Analogs bearing an aryl substituent at the 4-position of the coumarin core are synthesized according to the procedure outlined in Scheme 2. A cinnamic acid derivative, 2, is treated with resorcinol (3) in the presence of trifluoroacetic acid (TFA) under refluxing conditions to yield cyclized product 4, which is subsequently oxidized with 2,3-dichloro-5,6-dicyanobenzoquinone (DDQ) in an inert solvent which includes dioxane to give the desired coumarin intermediate 5 (see methods in Mezheritskii, V. V. et al. (2006) and Jagdale and Sudalai (2008)). Coumarin intermediate 5 is then alkylated with an alkyl halide R$^1$X in the presence of potassium iodide and potassium carbonate in an inert solvent which includes acetone to yield a coumarin 6 having aryl substituents in the 4-position (see methods in Van Camp, J. A. et al. (2007)).

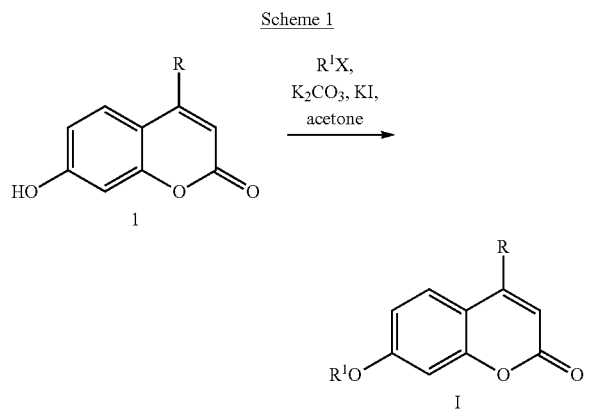

Synthesis and Data for Select Coumarin Compounds

Melting points were determined on a Mel-Temp II Laboratory Devices apparatus and are reported uncorrected. $^1$H NMR and $^{13}$C NMR spectra were recorded on an Agilent 400-MR 400-MHz NMR spectrometer. Chemical shifts are reported in parts per million using the residual proton or carbon signal ((CD$_3$)$_2$CO: $\delta_H$ 2.05, $\delta_c$ 29.84) as an internal reference. The apparent multiplicity (s=singlet, d=doublet, t=triplet, q=quartet, m=multiplet) and coupling constants (in Hz) are reported in that order in the parentheses after the chemical shift. Liquid chromatography and mass spectrometry were performed on a Shimadzu LCMS-2010 liquid chromatograph-mass spectrometer. High-resolution mass spectrometry was done by Dr. Yasuhiro Itagaki at Columbia University. Elemental analyses were performed by Atlantic Microlab, Inc. (Norcross, Ga.). The below compounds were made according to the methods described and referenced in Scheme 1 above.

3 (AKR 122/CHEMBRIDGE 6946484): mp: 101.5-103.0° C.; 1H NMR (400 MHz, (CD3)2CO): δ 7.69 (d, J=8.8 Hz, 1H), 7.02 (dd, J=8.8 Hz, J=2.4 Hz, 1H), 6.97 (d, J=2.4 Hz, 1H), 6.84 (s, 2H), 6.13 (q, J=1.2 Hz, 1H) 5.18 (s, 2H), 3.84 (s, 6H), 3.73 (s, 3H), 2.44 (d, J=1.2 Hz, 3H); 13C NMR (101 MHz, (CD3)2CO): δ 154.6, 127.1, 114.5, 113.5, 112.5, 106.2, 102.5, 71.3, 60.5, 56.5, 18.5; LC-MS (M$^+$-H): 355.

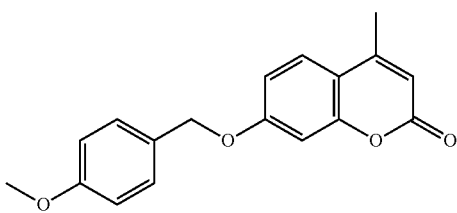 [SMILES: COc1ccc(COc2ccc3c(C)cc(=O)oc3c2)cc1]

3A (AKR-142): mp: 113.0-115.0° C.; 1H NMR (400 MHz, (CD3)2CO): δ 7.67 (d, J=8.8 Hz, 1H), 7.44 (d, J=8.8 Hz, 2H), 7.01-6.95 (m, 4H), 6.12 (q, J=1.2 Hz, 1H) 5.18 (s, 2H), 3.81 (s, 3H), 2.43 (d, J=1.2 Hz, 3H); 13C NMR (101 MHz, (CD3)2CO): δ 162.9, 160.9, 160.7, 153.7, 130.4, 129.4, 127.0, 114.8, 114.4, 113.5, 112.4, 102.4, 70.9, 55.6, 18.5; LC-MS (M+-H): 295; analysis (calcd., found for C18H16O4): C (72.96, 72.68), H (5.44, 5.57).

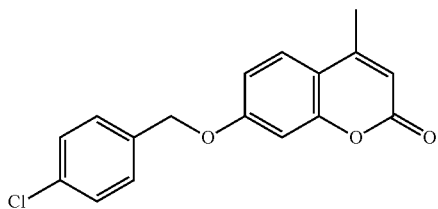 [SMILES: Cc1cc(=O)oc2cc(OCc3ccc(Cl)cc3)ccc12]

3B (AKR-146): (400 MHz, (CD3)2CO): δ 7.69 (d, J=8.8 Hz, 1H), 7.55 (d, J=8.4 Hz 2H), 7.45 (dt, J=8.4 Hz, J=2.4 Hz, 2H), 7.02 (dd, J=8.8 Hz, J=2.4 Hz, 1H), 6.97 (d, J=2.4 Hz, 1H), 6.13 (q, J=1.2 Hz, 1H) 5.28 (s, 2H), 2.44 (d, J=1.6 Hz, 3H); 13C NMR (101 MHz, (CD3)2CO): δ 162.5, 160.8, 153.6, 136.6, 134.3, 130.3, 129.5, 127.1, 114.7, 113.4, 112.6, 102.6, 70.2, 18.5.

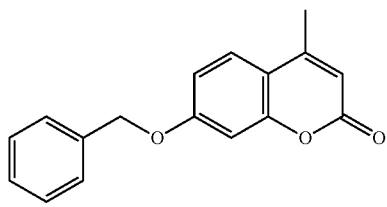 [SMILES: Cc1cc(=O)oc2cc(OCc3ccccc3)ccc12]

3C (AKR-121): mp: 118.0-118.5° C. (lit.ref 129-130° C.); 1H NMR (400 MHz, (CD3)2CO): δ 7.69 (d, J=9.2 Hz, 1H), 7.52 (d, J=7.2 Hz, 2H), 7.42 (tt, J=7.2 Hz, J=1.2 Hz, 2H), 7.35 (tt, J=7.2 Hz, J=1.2 Hz, 1H), 7.02 (dd, J=8.8 Hz, J=2.4 Hz, 1H), 6.97 (d, J=2.4 Hz, 1H), 6.13 (q, J=1.2 Hz, 1H) 5.27 (s, 2H), 2.44 (d, J=1.6 Hz, 3H); 13C NMR (101 MHz, (CD3)2CO): δ 162.8, 160.8, 156.3, 153.7, 137.6, 129.4, 128.9, 128.6, 127.1, 114.5, 113.5, 112.5, 102.6, 71.1, 18.5; LC-MS (M+-H): 265; analysis (calcd., found for C17H14O3): C (76.68, 76.51), H (5.30, 5.30).

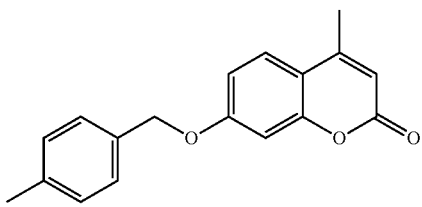 [SMILES: Cc1ccc(COc2ccc3c(C)cc(=O)oc3c2)cc1]

3D (AKR-124): 1H NMR (400 MHz, (CD3)2CO): δ 7.68 (d, J=8.8 Hz, 1H), 7.39 (d, J=8.0 Hz 2H), 7.23 (d, J=7.6 Hz), 7.00 (dd, J=8.8 Hz, J=2.4 Hz, 1H), 6.95 (d, J=2.4 Hz, 1H), 6.12 (q, J=1.2 Hz, 1H), 5.21 (s, 2H), 2.43 (d, J=1.2 Hz, 3H), 2.34 (s, 3H); 13C NMR (101 MHz, (CD3)2CO): δ 162.8, 160.8, 156.3, 153.7, 134.5, 130.0, 128.7, 127.1, 114.5, 113.5, 112.5, 102.5, 71.0, 21.2, 18.5.

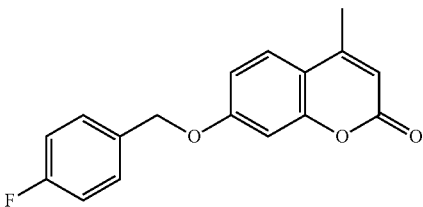 [SMILES: Cc1cc(=O)oc2cc(OCc3ccc(F)cc3)ccc12]

3E (AKR-144): 1H NMR (400 MHz, (CD3)2CO): δ 7.69 (d, J=8.8 Hz, 1H), 7.60-7.56 (m, 2H), 7.18 (tt, J=8.4 Hz, J=2.0 Hz, 2H), 7.02 (dd, J=8.8 Hz, J=2.4 Hz), 6.97 (d, J=2.0 Hz, 1H) 6.13 (q, J=1.2 Hz, 1H), 5.25 (s, 2H), 2.44 (d, J=1.2 Hz, 3H); 13C NMR (101 MHz, (CD3)2CO): δ 161.7, 152.7, 130.0, 129.9, 126.2, 115.3, 115.1, 112.5, 111.6, 101.6, 69.4, 17.6.

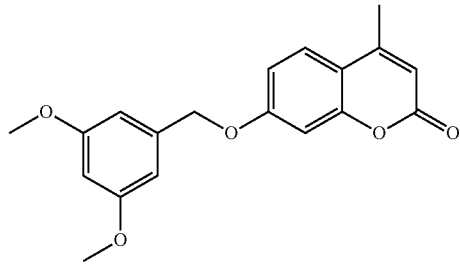 [SMILES: COc1cc(COc2ccc3c(C)cc(=O)oc3c2)cc(OC)c1]

3F (AKR-125): mp: 175.0-175.5 OC; 1H NMR (400 MHz, (CD3)2CO): δ 7.69 (d, J=9.2 Hz, 1H), 7.02 (dd, J=8.8 Hz, J=2.4 Hz), 6.95 (d, J=2.4 Hz, 1H), 6.67 (s, 2H), 6.46 (s, 1H), 6.13 (s, 1H), 5.21 (s, 2H), 3.79 (s, 6H), 2.44 (s, 3H); 13C NMR (101 MHz, (CD3)2CO): δ 162.1, 113.4, 112.5, 108.1, 106.2, 103.0, 100.4, 71.7, 55.6, 18.5; FAB+HRMS (m/z): [M]+ calcd. for C19H19O5: 327.1227. Found: 327.1237.

Two initial hits were identified: 2-(1-methyl-1H-indol-3-yl)-2-oxo-N-[4-(pyrrolidin-1-ylcarbonyl) phenyl]acetamide (ChemBridge #9039333 and with the scaffold of FIG. 3) and N-(4-chloro-3-[1,3]oxazolo[4,5-b]pyridin-2-ylphenyl)-2-thiophenecarboxamide (ChemBridge #9011680) (Formula III).

Figure 3:
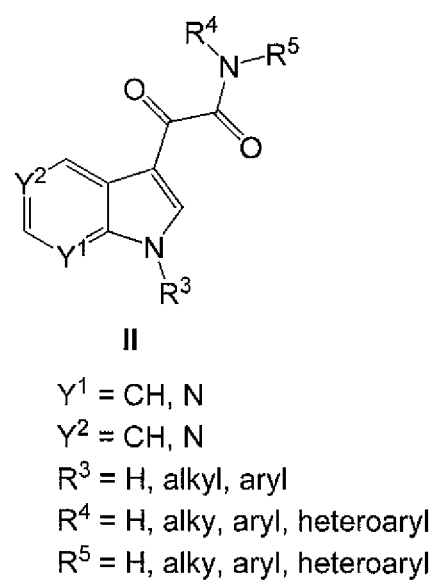
FIG. 3: General structure of the indole analogs.

As outlined in Scheme 3 indole analogs of the invention can be prepared via a synthetic route reported by Thompson et al. (2009) from commercially available 1-methylindole (7, $R^3$=CH$_3$) which in the presence of oxalyl chloride gives intermediate 8, which is then treated with the respective amine $R^4R^5$NH in the presence of N,N-diisopropylethylamine (Hünig's base) to afford 7H-pyrrolo[2,3-d]pyrimidines II, ($Y^1$=N, $Y^2$=N) (FIG. 3).

Scheme 3: Synthetic route for the preparation of the indole analogs.

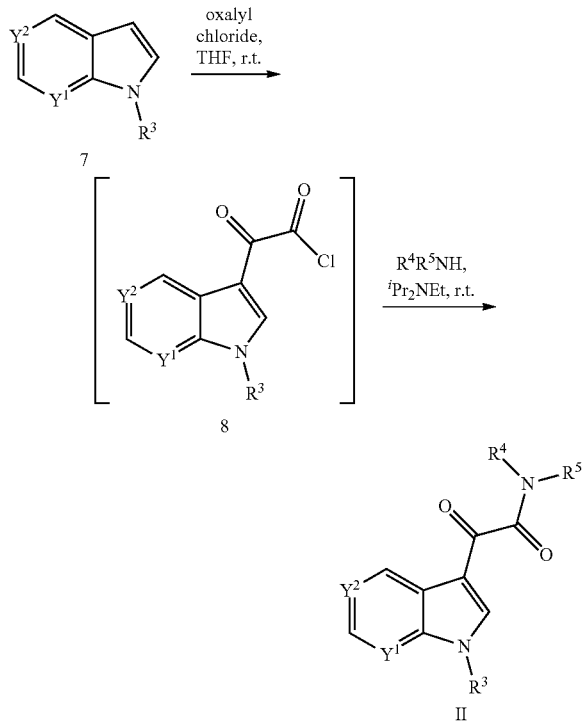

The Below Scheme Shows the Experimental Procedure for Making Compounds of Formula III

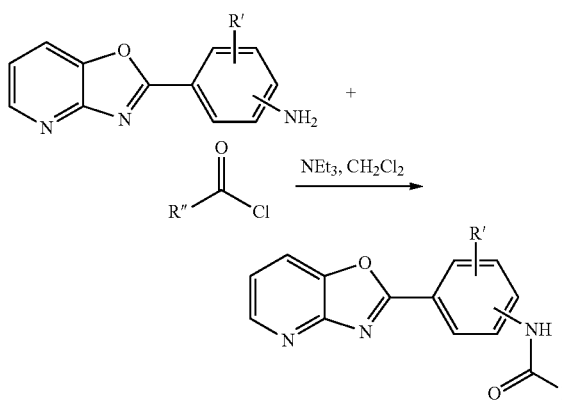

To a solution of a 4-oxazolo[4,5-b]pyridin-2-ylbenzenamine (1.5 equiv.) in methylene chloride at 0° C. is added first triethylamine (1.25-1.5 equiv.), then the aroyl chloride (1.0 equiv.).

Standard Pharmacological Validation Methods

Evaluation of representative compounds of this invention in several standard pharmacological test procedures indicated that the compounds of this invention possess significant activity for treating, preventing or inhibiting a parasite infection in a patient or subject or for inhibiting a parasite infection in a patient or subject.

The data described herein indicate that the PfENT1 inhibitory compounds described herein would be effective at treating or preventing avian malaria.

The data described herein indicate that the PfENT1 inhibitory compounds described herein would also be effective at treating or preventing infection or disease caused by other species of Plasmodium (including P. malariae, P. ovale, P. vivax and P. knowlesi), as well as Leishmania, Trypanosoma, Entamoeba, Giardia, Naegleria, and Trichomonas protozoa.

Herein a novel yeast-based high throughput screening assay has been used to identify compounds that inhibit PfENT1. Nine of the compounds were tested in two yeast based assays and both indicate that they inhibit PfENT1 transport activity. The ability of the subset of nine of the identified compounds to inhibit growth of P. falciparum parasites during in vitro culture was also confirmed. The compounds inhibit parasite growth. These compounds can serve as novel antimalarial drugs. PfENT1 inhibitors may also serve as a treatment for cerebral malaria as well as malaria prophylaxis for travelers.

Because malaria parasites develop resistance to antimalarial drugs there is an ongoing need to develop novel antimalarial drugs. A novel assay has been developed to identify equilibrative nucleoside transporter inhibitors. Using this assay a group of compounds have been identified that inhibit the Plasmodium falciparum equilibrative nucleoside transporter 1 (PfENT1). These compounds can be used as anti-malarial drugs.

Furthermore, recent studies in a mouse model of cerebral malaria, infection with P. berghei ANKA, showed that parasites with a knockout of the P. berghei ENT1 did not develop cerebral malaria. Thus, the compounds identified can treat cerebral malaria, which has a mortality of ~30%. In addition, people who travel to malaria endemic regions need to take prophylactic medicines to prevent contracting malaria. The compounds identified can serve as prophylactic drugs because the PfENT1 transporter is expressed in the asymptomatic initial hepatic stage of malaria infection. Inhibition of PfENT1 can prevent the extensive replication that occurs during the hepatic stage and can prevent or attenuate subsequent development of symptomatic blood stages of malaria.

EXAMPLE 1

Validation Results

A yeast-based high throughput screening (HTS) assay was used to identify compounds that inhibit PfENT1. The compounds described in this application were identified by screening four commercially available, chemical compound libraries obtained from Dr. Donald Landry's laboratory (Department of Medicine, Columbia University). These libraries contain approximately 80,000 unique chemical entities. Derivatives of the some of the initial hits were purchased from ChemBridge Corporation (11199 Sorrento Valley Road, Suite 206, San Diego, Calif., 92121) and other novel chemical entities have been synthesized and tested as well.

In the primary screen the compounds were tested at a concentration of 10 μM. Hits were identified by the growth of fui1Δ yeast expressing PfENT1 and Green Fluorescent Protein (GFP) in the presence of the cytotoxic nucleoside 5-fluorouridine (5-FUrd). 5-FUrd is transported by PfENT1. PfENT1 expressing fui1Δ yeast will only grow in the presence of 125 μM 5-FUrd if a PfENT1 inhibitor blocks the uptake of 5-FUrd into the yeast. Significant yeast growth in the HTS in 384 well plates was determined by two criteria: 1) turbidity as determined by the optical density at 620 nm ($OD_{620}$) and 2) GFP fluorescence intensity. Positive responses were signal intensities greater than four standard deviations above the mean of the negative growth control wells. Hits had to be positive by both criteria. From the library screen, 171 chemical entities were identified as positive by both criteria (Table 2).

Of the 171 hits from the primary HTS, nine were chosen for more extensive validation using a series of secondary assays. These nine compounds included the top seven hits (HTS rank #1-7 as indicated in Tables 1 and 2), the first hit identified (compound HTS rank #19) and compound HTS rank #13, which was a unique chemical scaffold relative to the other 8 compounds. The secondary assays used to validate the nine selected hits include 1) repeat of the primary HTS using a series of compound concentrations to determine the concentration-response relationship for each compound, 2) testing in an alternative yeast-based assay in purine auxotrophic ade2Δ yeast expressing PfENT1 (described below, FIG. 1 and FIG. 4B), and 3) a *Plasmodium falciparum* cytotoxicity assay (described below, FIGS. 5A-B.). These assays allowed further confirmation the hits, determining the concentration-response relationships in the yeast-based assays and the concentration dependence of their ability to kill *Plasmodium falciparum* parasites during growth in in vitro culture. There was a roughly linear correlation between the compounds' $IC_{50}$s measured in the two yeast-based assays. All nine compounds were tested in the *P. falciparum* cytotoxicity assay (FIGS. 5A-B). All of the Table 1 compounds inhibited parasite growth with an $IC_{50}$ between ~3-50 μM (FIGS. 5A-B). Additionally, FIG. 5D shows Geimsa stained cultures illustrating parasite morphology for cultures treated with 10 times the $IC_{50}$ concentration of compound 3 (ChemBridge #6946484) compared to DMSO treated *P. falciparum* 3D7 cultures at the indicated times. FIG. 5E shows graphs illustrating DNA quantification for compound 3 (ChemBridge #6946484) compared to DMSO treated *P. falciparum* 3D7 cultures at the indicated times.

Additionally, FIG. 5C shows concentration-dependent inhibition of [$^3$H]adenosine uptake into trophozoite-stage *P. falciparum* 3D7 culture over 15 minutes with the nine selected compounds shown in Table 1.

Alternative yeast-based assay in purine auxotrophic ade2Δ yeast: The alternative assay relies on the ability of PfENT1 to transport adenosine. Yeast lack the capacity to transport adenosine into the cell. Purine auxotrophic yeast were generated by a knockout of the yeast ade2 gene (ade2Δ), an essential enzyme in the yeast de novo purine biosynthetic pathway. These purine auxotrophic ade2Δ yeast can grow on adenine imported by endogenous yeast nucleobase transporters but cannot grow on the nucleoside adenosine because yeast lack the ability to transport adenosine. Expression of PfENT1, which can transport adenosine, allows ade2Δ yeast to grow in the presence of adenosine. FIG. 1 is a graph showing the concentration-response relationship for the ChemBridge compounds #9039333 and #9011680 using growth inhibition of PfENT1-expressing ade2Δ yeast.

FIG. 4A shows the concentration-dependent rescue of PfENT1-HA-CO-expressing fui1Δ yeast from 5-FUrd induced death with the nine compounds from Table 1. FIG. 4B shows the concentration-dependent growth inhibition of purine auxotrophic yeast expressing PfENT1-CO in adenosine medium with the nine compounds from Table 1. FIG. 4C shows the concentration-dependent inhibition of [$^3$H]adenosine uptake into PfENT1-CO expressing yeast over 15 minutes with the compounds from Table 1. The means values from single experiments are shown. In the key, CQ=chloroquine, and the Table 1 compounds are referenced as symbols indicating HTS rank #1-7, 13, and 19. In this assay, inhibitors of PfENT1 prevent yeast growth (FIGS. 4B-C).

*Plasmodium falciparum* Cytotoxicity Assay

*P. falciparum* parasites (3D7 strain-chloroquine sensitive) are grown in in vitro culture in human erythrocytes. Each well is inoculated with a low density of parasites in standard parasite growth media with supplemented hypoxanthine (10 or 367 μM). Increasing concentrations of drugs are added and parasites are allowed to grow for 72-96 hours in 5% $CO_2$/5% $O_2$/90% $N_2$ gas at 37° C. At the end of the experiment, parasites are lysed, SYBR-Green dye in lysis solution is added and the fluorescence intensity is measured for each well.

A summary of the parasite growth inhibition results for the nine selected compounds is provided in Table 3.

TABLE 3

Summary Data showing Structures and $IC_{50}$s in the parasite growth assays for the nine compounds selected from the HTS.

| HTS Rank # | Structure | Compound Name Chem Bridge # | $IC_{50}$ 3D7 parasite viability- low purine media (μM) | $IC_{50}$ 3D7 parasite viability- high purine media (μM) | $IC_{50}$ Dd2 parasite viability- high purine media (μM) |
|---|---|---|---|---|---|
| 1 | (structure) | N,N'-1,3-benzothiazole-2,6-diyldi(2-furamide) 9001893 | 31.1 ± 4.7 | 37.7 ± 2.0 | 25.8 ± 1.3 |

TABLE 3-continued

Summary Data showing Structures and IC$_{50}$s in the parasite growth assays
for the nine compounds selected from the HTS.

| HTS Rank # | Structure | Compound Name Chem Bridge # | IC$_{50}$ 3D7 parasite viability- low purine media (µM) | IC$_{50}$ 3D7 parasite viability- high purine media (µM) | IC$_{50}$ Dd2 parasite viability- high purine media (µM) |
|---|---|---|---|---|---|
| 2 | 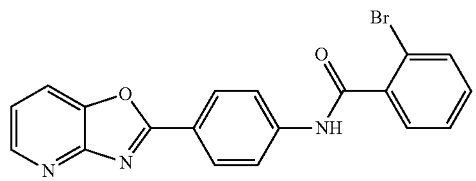 [SMILES: O=C(Nc1ccc(-c2nc3ncccc3o2)cc1)c1ccccc1Br] | 2-bromo-N-(4-[1,3]oxazolo[4,5-b]pyridin-2-ylphenyl)benzamide 6718896 | 31.2 ± 7.7 | 53.4 ± 11.1 | 52.4 ± 5.7 |
| 3 | 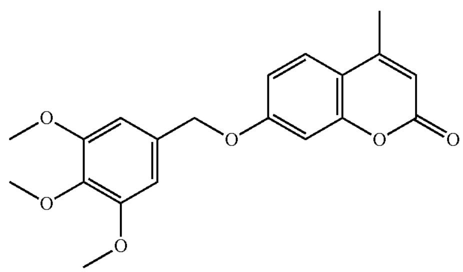 [SMILES: COc1cc(COc2ccc3c(C)cc(=O)oc3c2)cc(OC)c1OC] | 4-methyl-7-[(3,4,5-trimethoxybenzyl)oxy]-2H-chromen-2-one 6946484 | 19.2 ± 4.3 | 41.0 ± 4.3 | 36.2 ± 6.0 |
| 4 | 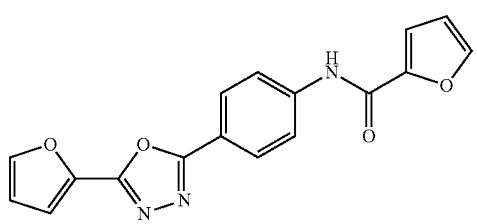 [SMILES: O=C(Nc1ccc(-c2nnc(-c3ccco3)o2)cc1)c1ccco1] | N-{4-[5-(2-furyl)-1,3,4-oxadiazol-2-yl]phenyl}-2-furamide 6081106 | 15.0 ± 1.5 | 14.7 ± 1.9 | 15.3 ± 2.7 |
| 5 | 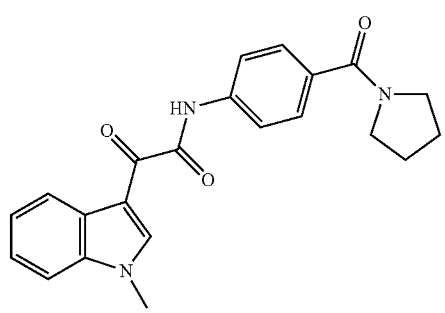 [SMILES: Cn1cc(C(=O)C(=O)Nc2ccc(C(=O)N3CCCC3)cc2)c2ccccc21] | 2-(1-methyl-1H-indol-3-yl)-2-oxo-N-[4-(pyrrolidin-1-ylcarbonyl)phenyl]acetamide 9039333 | 35.5 ± 0.7 | 33.1 ± 0.5 | 28.9 ± 2.6 |
| 6 | 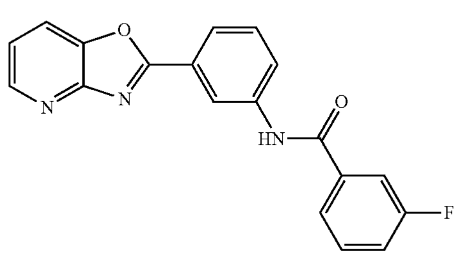 [SMILES: O=C(Nc1cccc(-c2nc3ncccc3o2)c1)c1cccc(F)c1] | 3-fluoro-N-(3-[1,3]oxazolo[4,5-b]pyridin-2-ylphenyl)benzamide 9011026 | 34.8 ± 2.4 | 33.7 ± 5.0 | 38.8 ± 4.9 |

TABLE 3-continued

Summary Data showing Structures and IC$_{50}$s in the parasite growth assays for the nine compounds selected from the HTS.

| HTS Rank # | Structure | Compound Name Chem Bridge # | IC$_{50}$ 3D7 parasite viability-low purine media (µM) | IC$_{50}$ 3D7 parasite viability-high purine media (µM) | IC$_{50}$ Dd2 parasite viability-high purine media (µM) |
|---|---|---|---|---|---|
| 7 | 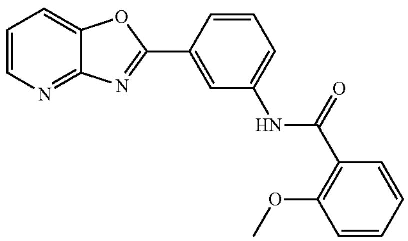 [SMILES: COc1ccccc1C(=O)Nc1cccc(-c2nc3ncccc3o2)c1] | 2-methoxy-N-(3-[1,3]oxazolo[4,5-b]pyridin-2-ylphenyl)benzamide 6736283 Encompassed by Formula III | 43.6 ± 4.4 | 44.8 ± 3.8 | 31.0 ± 0.6 |
| 13 | 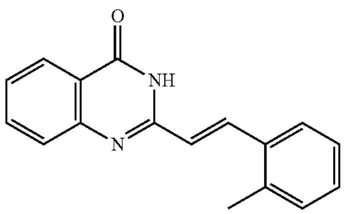 [SMILES: Cc1ccccc1/C=C/c1nc2ccccc2c(=O)[nH]1] | 2-[2-(2-methylphenyl)vinyl]-4(3H)-quinazolinone 6517398 | 6.9 ± 0.4 | 6.7 ± 0.5 | 2.6 ± 0.2 |
| 19 | 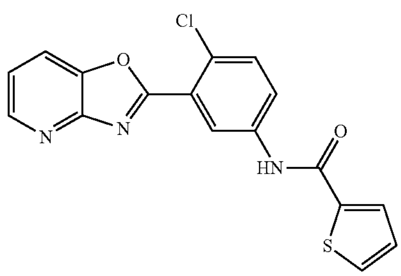 [SMILES: O=C(Nc1ccc(Cl)c(-c2nc3ncccc3o2)c1)c1cccs1] | N-(4-chloro-3-[1,3]oxazolo[4,5-b]pyridin-2-ylphenyl)-2-thiophenecarboxamide 9011680 | 43.2 ± 2.9 | 42.9 ± 2.8 | 37.4 ± 1.6 |

Mean ± SD are shown, N ≥ 3 biological replicates for all data.

Certain methods relating to the secondary assays are well-known and are found in the following references.

Iversen, P. W. et al. HTS Assay Validation. in *Assay Guidance Manual* (eds. Sittampalam, G. S. et al.) (Bethesda Md., 2004).

Winzeler, E. A. et al. Functional characterization of the *S. cerevisiae* genome by gene deletion and parallel analysis. Science 285, 901-6 (1999).

Janke, C. et al. A versatile toolbox for PCR-based tagging of yeast genes: new fluorescent proteins, more markers and promoter substitution cassettes. Yeast 21, 947-62 (2004).

Gari, E., Piedrafita, L., Aldea, M. & Herrero, E. A set of vectors with a tetracycline-regulatable promoter system for modulated gene expression in *Saccharomyces cerevisiae*. Yeast 13, 837-48 (1997).

Riegelhaupt, P. M. et al. Transport of purines and purine salvage pathway inhibitors by the *Plasmodium falciparum* equilibrative nucleoside transporter PfENT1. Mol. Biochem. Parasitol. 169, 40-9 (2010).

Westermann, B. & Neupert, W. Mitochondria-targeted green fluorescent proteins: convenient tools for the study of organelle biogenesis in *Saccharomyces cerevisiae*. Yeast 16, 1421-7 (2000).

Hill, J., Donald, K. A. & Griffiths, D. E. DMSO-enhanced whole cell yeast transformation. Nucleic Acids Res. 19, 5791 (1991).

Sheff, M. A. & Thorn, K. S. Optimized cassettes for fluorescent protein tagging in *Saccharomyces cerevisiae*. Yeast 21, 661-70 (2004).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

ADDITIONAL REFERENCES

Baldwin S A, Beal P R, Yao S Y, King A E, Cass C E, et al. (2004) The equilibrative nucleoside transporter family, SLC29. Pflugers Arch 447: 735-743.

Pastor-Anglada M, Cano-Soldado P, Errasti-Murugarren E, Casado F J (2008) SLC28 genes and concentrative nucleoside transporter (CNT) proteins. Xenobiotica 38: 972-994.

Carter N S, Yates P, Arendt C S, Boitz J M, Ullman B (2008) Purine and pyrimidine metabolism in *Leishmania*. Adv Exp Med Biol 625: 141-154.

Landfear S M, Ullman B, Carter N S, Sanchez M A (2004) Nucleoside and nucleobase transporters in parasitic protozoa. Eukaryot Cell 3: 245-254.

Cass C E, Young J D, Baldwin S A (1998) Recent advances in the molecular biology of nucleoside transporters of mammalian cells. Biochem Cell Biol 76: 761-770.

Cass C E, Young J D, Baldwin S A, Cabrita M A, Graham K A, et al. (1999) Nucleoside transporters of mammalian cells. Pharm Biotechnol 12: 313-352.

Cassera M B, Zhang Y, Hazleton K Z, Schramm V L (2011) Purine and pyrimidine pathways as targets in *Plasmodium falciparum*. Current topics in medicinal chemistry 11: 2103-2115.

El Bissati K, Zufferey R, Witola W H, Carter N S, Ullman B, et al. (2006) The plasma membrane permease PfNT1 is essential for purine salvage in the human malaria parasite *Plasmodium falciparum*. Proc Natl Acad Sci USA 103: 9286-9291.

Mlambo G, Kumar N. (2008). "Transgenic rodent *Plasmodium berghei* parasites as tools for assessment of functional immunogenicity and optimization of human malaria vaccines". Eukaryotic Cell 7 (11): 1875-9.

Mueller I, Zimmerman P A, Reeder J C (2007). "*Plasmodium malariae* and *Plasmodium ovale*—the "bashful" malaria parasites". Trends in Parasitology 23 (6): 278-83.

Collins W E (2012). "*Plasmodium knowlesi*: A malaria parasite of monkeys and humans". Annual Review of Entomology 57: 107-21.

Nadjm B, Behrens R H (2012). "Malaria: An update for physicians". Infectious Disease Clinics of North America 26 (2): 243-59.

Sarkar P K, Ahluwalia G, Vijayan V K, Talwar A (2009). "Critical care aspects of malaria". Journal of Intensive Care Medicine 25 (2): 93-103.

Baird J K (2013). "Evidence and implications of mortality associated with acute *Plasmodium vivax* malaria". Clinical Microbiology Reviews 26 (1): 36-57.

Arnott A, Barry A E, Reeder J C (2012). "Understanding the population genetics of *Plasmodium vivax* is essential for malaria control and elimination". Malaria Journal 11: 14.

Thompson, M J, Borsenberger, V, Louth, J C, Judd, K E, Chen, B (2009). "Design, Synthesis, and Structure-Activity Relationship of Indole-3-glyoxylamide Libraries Possessing Highly Potent Activity in a Cell Line Model of Prion Disease". Journal of Medicinal Chemistry 52 (23): 7503-7511.

Lévai, A. & Jekö, J. An efficient procedure for the preparation of 4-methyl-2-thiocoumarins by the reaction of 4-methylcoumarins with Lawesson's reagent. J. Heterocyclic Chem. 42, 739-742 (2005).

Mezheritskii, V. V. et al. Polynuclear heterocyclic systems based on naphthalene-1,5-diol. I. Reaction of naphthalene-1,5-diol and its derivatives with β-dicarbonyl and α,β-unsaturated carbonyl compounds, Russ. J. Org. Chem. 42, 1458-1463 (2006).

Jagdale, A. R. & Sudalai, A., Co-catalyzed mild and chemoselective reduction of phenyl esters with NaBH4: a practical synthesis of (R)-tolterodine. Tetrahedron Lett. 49, 3790-3793 (2008).

Van Camp, J. A. et al., Preparation of 4-aryl-2-trifluoromethylbenzonitrile derivatives as androgen receptor antagonists for topical suppression of sebum production. Bioorg. Med. Chem. Lett. 17, 5529-5532 (2007).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method for inhibiting an Equilibrative Nucleoside Transporter (ENT) of a *Plasmodium* species comprising contacting the *Plasmodium* species with 2-[2-(2-methylphenyl)vinyl]-4(3H)-quinazolinone, or a pharmaceutically acceptable salt thereof, in an amount effective to inhibit the ENT of the *Plasmodium* species.

2. The method of claim 1, wherein the ENT is an ENT1, ENT2, ENT3, or ENT4.

3. The method of claim 2, wherein the ENT is an ENT1.

4. The method of claim 1, wherein plasmodium species is *P. falciparum, P. berghei, P. vivax, P. ovale, P. malariae* or *P. knowlesi*.

5. The method of claim 4, wherein the *plasmodium* species is *Plasmodium falciparum*.

6. A method of treatment or prophylaxis of a disorder or disease mediated by infection with a parasitic purine auxotroph, comprising administering to a patient in need thereof a therapeutically effective amount of the compound of 2-[2-(2-methylphenyl)vinyl]-4(3H)-quinazolinone, or a pharmaceutically acceptable salt thereof.

7. The method of claim 6, wherein the disorder or disease is malaria.

8. The method of claim 6, wherein the disorder or disease is one or more of those selected from the group consisting of malaria, leishmaniasis, African sleeping sickness, Chagas disease, and toxoplasmosis.

9. The method of claim 6, wherein the patient is a mammal.

* * * * *